(12) United States Patent
Hayakawa et al.

(10) Patent No.: US 7,176,219 B2
(45) Date of Patent: Feb. 13, 2007

(54) SALTS OF QUINUCLIDINE DERIVATIVE

(75) Inventors: Masahiko Hayakawa, Tsukuba (JP); Kiyohiro Samizu, Tsukuba (JP); Hiroshi Uebayashi, Tsukuba (JP); Ken Ikeda, Tsukuba (JP); Makoto Takeuchi, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/128,238

(22) Filed: May 13, 2005

(65) Prior Publication Data

US 2006/0205770 A1 Sep. 14, 2006

(30) Foreign Application Priority Data

Mar. 8, 2005 (JP) ............ P. 2005-063405
Mar. 25, 2005 (JP) ............ P. 2005-088872

(51) Int. Cl.
*A61K 31/44* (2006.01)
(52) U.S. Cl. ............... 514/305; 546/137
(58) Field of Classification Search ......... 514/305; 546/137

See application file for complete search history.

(56) References Cited

U.S. PATENT DOCUMENTS 6,017,917 A 1/2000 Kuno et al.

FOREIGN PATENT DOCUMENTS

| EP | 0 801 067 A1 | 10/1997 |
|---|---|---|
| JP | 3701964 | 4/1991 |
| JP | 10/007675 | 1/1998 |
| JP | 2002/104968 | 4/2002 |
| WO | WO 1996/020194 | 7/1996 |

OTHER PUBLICATIONS

International Search Rreport for PCT/JP2006/304241.

*Primary Examiner*—Amelia A. Owens
(74) *Attorney, Agent, or Firm*—Sughrue Mion, PLLC

(57) ABSTRACT

There is provided an acid addition salt of (−)-(3R)-quinuclidin-3-yl(1R)-1-phenyl-1,2,3,4-tetrahydroisoquinoline-2-carboxylate with an acid selected from the group consisting of (−)-(2S,3S)-tartaric acid, (+)-(2S,3S)-di-O-benzoyltartaric acid, (+)-(2S,3S)-di-O-(4-methylbenzoyl)tartaric acid, (−)-L-phenylalanine, benzenesulfonic acid, cyclohexanesulfamic acid, hydrobromic acid, naphthalene-2-sulfonic acid, sebacic acid, (+)-camphor-10-sulfonic acid, p-toluenesulfonic acid, ethanesulfonic acid, methanesulfonic acid and methyl phosphate, which has little hygroscopicity that affects the use as a drug or its drug substance, and is very useful as a drug or its drug substance.

16 Claims, 31 Drawing Sheets

SALTS OF QUINUCLIDINE DERIVATIVE

TECHNICAL FIELD

The present invention relates to novel acid addition salts of (−)-(3R)-quinuclidin-3-yl(1R)-1-phenyl-1,2,3,4-tetrahydroisoquinoline-2-carboxylate (hereinafter referred to as Compound A) which are useful as drugs, particularly as muscarine $M_3$ receptor antagonists.

BACKGROUND ART

It was made public that Compound A having the chemical formula shown as below, since it displays an affinity and selectivity for muscarinic $M_3$ receptors, is useful as an $M_3$ receptor antagonist in prophylaxis or treatment of various $M_3$ receptor-mediated diseases, particularly, urologic diseases such as urinary incontinence or pollakisuria in neurotic pollakisuria, neurogenic bladder, nocturnal enuresis, unstable bladder, bladder spasm, chronic cystitis, etc., respiratory diseases such as chronic obstructive pulmonary disease, chronic bronchitis, asthma and rhinitis, or digestive tract diseases such as irritable bowel syndrome also referred to as spastic colitis or diverticulitis (Patent document 1).

Compound A

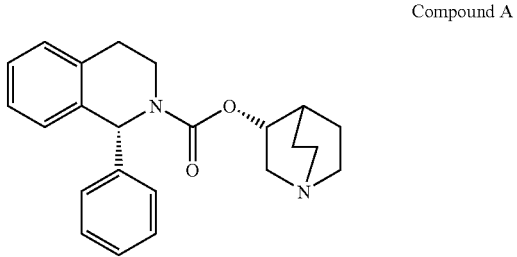

For the acid addition salt of Compound A, the above patent document 1 discloses only one salt, the hydrochloride salt of Compound A in Example 10, and no particular example is known regarding other acid addition salts except the hydrochloride salt described in the above patent document 1.

[Patent document 1] EP 0 801 067

DISCLOSURE OF INVENTION

The Compound A hydrochloride, only one known acid addition salt of Compound A, can be obtained as a crystalline anhydride, but it has been found that the hydrochloride is so hygroscopic as to deliquesce in a conventional environment kept at a relative humidity of 70% (room temperature) and accompanied by increase of impurities during long-term storage.

In order to supply a safer pharmaceutical preparation or its drug substance, accordingly, it has been desired that a lesser hygroscopic salt of Compound A, particularly the salt highly stable to humidity, other than the hydrochloride could be discovered.

The present inventors have investigated a variety of acid addition salts of Compound A and found that particular acid addition salts of Compound A are less hygroscopic and have higher stability to humidity than the conventional hydrochloride salt. Thus, the invention was completed. According to the invention, there is provided acid addition salt of Compound A with an acid selected from the group S consisting of (−)-(2S,3S)-tartaric acid, (+)-(2S,3S)-di-O-benzoyltartaric acid, (+)-(2S,3S)-di-O-(4-methylbenzoyl) tartaric acid, (−)-L-phenylalanine, benzenesulfonic acid, cyclohexanesulfamic acid, hydrobromic acid, naphthalene-2-sulfonic acid, sebacic acid, (+)-camphor-10-sulfonic acid, p-toluenesulfonic acid, ethanesulfonic acid, methanesulfonic acid and methyl phosphate.

Concretely, the invention provides an acid addition salt of (−)-(3R)-quinuclidin-3-yl(1R)-1-phenyl-1,2,3,4-tetrahydroisoquinoline-2-carboxylate, i.e., Compound A, selected from (−)-(3R)-quinuclidin-3-yl(1R)-1-phenyl-1,2,3,4-tetrahydroisoquinoline-2-carboxylate (−)-(2S,3S)-tartrate, (−)-(3R)-quinuclidin-3-yl(1R)-1-phenyl-1,2,3,4-tetrahydroisoquinoline-2-carboxylate (+)-(2S,3S)-di-O-benzoyltartrate, (−)-(3R)-quinuclidin-3-yl(1R)-1-phenyl-1,2,3,4-tetrahydroisoquinoline-2-carboxylate (+)-(2S,3S)-di-O-(4-methylbenzoyl)tartrate, (−)-(3R)-quinuclidin-3-yl(1R)-1-phenyl-1,2,3,4-tetrahydroisoquinoline-2-carboxylate (−)-L-phenylalaninate, (−)-(3R)-quinuclidin-3-yl(1R)-1-phenyl-1,2,3,4-tetrahydroisoquinoline-2-carboxylate benzenesulfonate, (−)-(3R)-quinuclidin-3-yl(1R)-1-phenyl-1,2,3,4-tetrahydroisoquinoline-2-carboxylate cyclohexanesulfamate, (−)-(3R)-quinuclidin-3-yl(1R)-1-phenyl-1,2,3,4-tetrahydroisoquinoline-2-carboxylate hydrobromide, (−)-(3R)-quinuclidin-3-yl(1R)-1-phenyl-1,2,3,4-tetrahydroisoquinoline-2-carboxylate naphthalene-2-sulfonate, (−)-(3R)-quinuclidin-3-yl(1R)-1-phenyl-1,2,3,4-tetrahydroisoquinoline-2-carboxylate sebacate, (−)-(3R)-quinuclidin-3-yl(1R)-1-phenyl-1,2,3,4-tetrahydroisoquinoline-2-carboxylate (+)-camphor-10-sulfonate, (−)-(3R)-quinuclidin-3-yl(1R)-1-phenyl-1,2,3,4-tetrahydroisoquinoline-2-carboxylate p-toluenesulfonate, (−)-(3R)-quinuclidin-3-yl(1R)-1-phenyl-1,2,3,4-tetrahydroisoquinoline-2-carboxylate ethanesulfonate, (−)-(3R)-quinuclidin-3-yl(1R)-1-phenyl-1,2,3,4-tetrahydroisoquinoline-2-carboxylate methanesulfonate, and (−)-(3R)-quinuclidin-3-yl(1R)-1-phenyl-1,2,3,4-tetrahydroisoquinoline-2-carboxylate methyl phosphate.

Among these salts, the preferred one is (−)-(3R)-quinuclidin-3-yl(1R)-1-phenyl-1,2,3,4-tetrahydroisoquinoline-2-carboxylate (−)-(2S,3S)-tartrate; in another aspect, the preferred one is (−)-(3R)-quinuclidin-3-yl(1R)-1-phenyl-1,2,3,4-tetrahydroisoquinoline-2-carboxylate (+)-(2S,3S)-di-O-benzoyltartrate; in another aspect, the preferred one is (−)-(3R)-quinuclidin-3-yl(1R)-1-phenyl-1,2,3,4-tetrahydroisoquinoline-2-carboxylate (+)-(2S,3S)-di-O-(4-methylbenzoyl)tartrate; in another aspect, the preferred one is (−)-(3R)-quinuclidin-3-yl(1R)-1-phenyl-1,2,3,4-tetrahydroisoquinoline-2-carboxylate (−)-L-phenylalaninate; in another aspect, the preferred one is (−)-(3R)-quinuclidin-3-yl(1R)-1-phenyl-1,2,3,4-tetrahydroisoquinoline-2-carboxylate benzenesulfonate; in another aspect, the preferred one is (−)-(3R)-quinuclidin-3-yl(1R)-1-phenyl-1,2,3,4-tetrahydroisoquinoline-2-carboxylate cyclohexanesulfamate; in another aspect, the preferred one is (−)-(3R)-quinuclidin-3-yl(1R)-1-phenyl-1,2,3,4-tetrahydroisoquinoline-2-carboxylate hydrobromide; in another aspect, the preferred one is (−)-(3R)-quinuclidin-3-yl(1R)-1-phenyl-1,2,3,4-tetrahydroisoquinoline-2-carboxylate naphthalene-2-sulfonate; in another aspect, the preferred one is (−)-(3R)-quinuclidin-3-yl(1R)-1-phenyl-1,2,3,4-tetrahydroisoquinoline-2-carboxylate sebacate; in another aspect, the preferred one is (−)-(3R)-quinuclidin-3-yl(1R)-1-phenyl-1,2,3,4-tetrahydroisoquinoline-2-carboxylate (+)-camphor-10-sulfonate; in another aspect, the preferred one is (−)-(3R)-quinuclidin-3-yl(1R)-1-phenyl-1,2,3,4-tetrahydroisoquinoline-2-carboxylate p-toluenesulfonate; in another aspect, the preferred one is (−)-(3R)-quinuclidin-3-yl(1R)-1-phenyl-1,2,3,4-tetrahydroisoquinoline-2-carboxylate ethanesulfonate; in another aspect, the preferred one is (−)-(3R)-quinuclidin-3-yl(1R)-1-phenyl-1,2,3,4-tetrahydroisoquinoline-2-carboxylate methanesulfonate; and in another aspect, the preferred one is (−)-(3R)-quinuclidin-3-yl(1R)-1-phenyl-1,2,3,4-tetrahydroisoquinoline-2-carboxylate methyl phosphate.

Indeed, cyclohexanesulfamic acid is also called cyclohexylsulfamic acid, sebacic acid is also called decandicarboxylic acid, (+)-camphor-10-sulfonic acid is also called (+)-[(1S,4R)-7,7-dimethyl-2-oxobicyclo[2.2.1]heptan-1-yl]methansulfonic acid, and p-toluenesulfonic acid is also called 4-methylbenzenesulfonic acid.

In addition, according to the invention, a pharmaceutical composition comprising as an active ingredient one or more acid addition salts of Compound A, i.e., (−)-(3R)-quinuclidin-3-yl(1R)-1-phenyl-1,2,3,4-tetrahydroisoquinoline-2-carboxylate, particularly being a muscarine $M_3$ receptor antagonist, is provided.

In the acid addition salts of the invention of Compound A with an acid selected from the above-mentioned group S, the hygroscopicity is improved and the stability to humidity is greatly enhanced in comparison with the known Compound A hydrochloride. Thus, the salts of the invention are very useful as drugs or their drug substances.

In particular, as commonly known, it is known that in hygroscopically improved drugs or their drug substances, the problems on storage at a humidity in storage conditions and on quality control are reduced, and additionally the problem on weight variations of the active ingredient in the pharmaceutical preparations during production of solid preparations such as tablets or capsules is also reduced. That is, the acid addition salts of Compound A of the invention are expected to show stable shelf life and easiness of quality control since they have improved hygroscopicity; thus, the salts may be considered to be easily handling compounds in pharmaceutical preparation and contribute to provide much better pharmaceutical preparations with high quality.

BEST MODE FOR CARRYING OUT THE INVENTION

Figure 1:
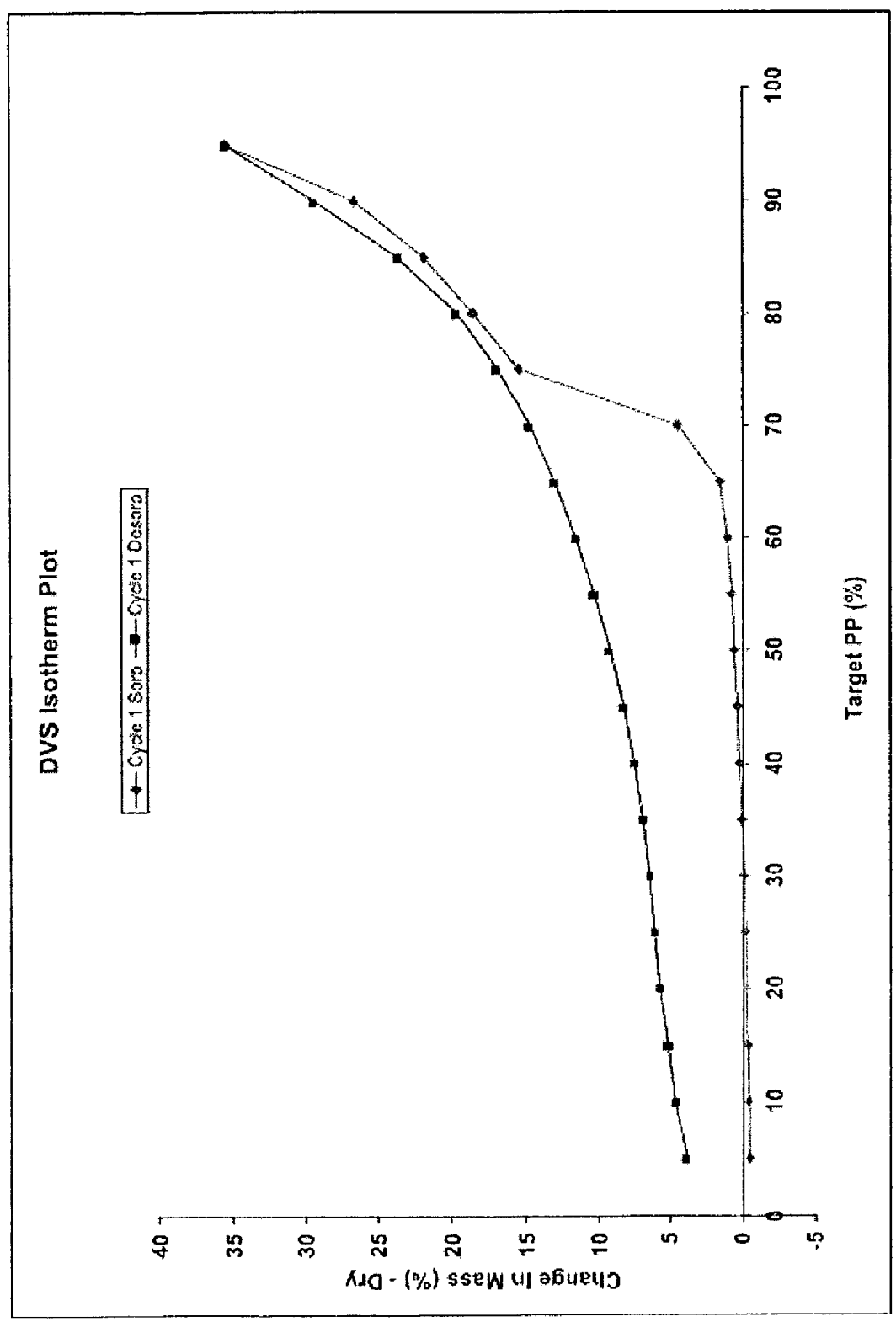
FIG. 1 shows an isothermal curve of water absorption and desorption in the known Compound A hydrochloride.
Figure 2:
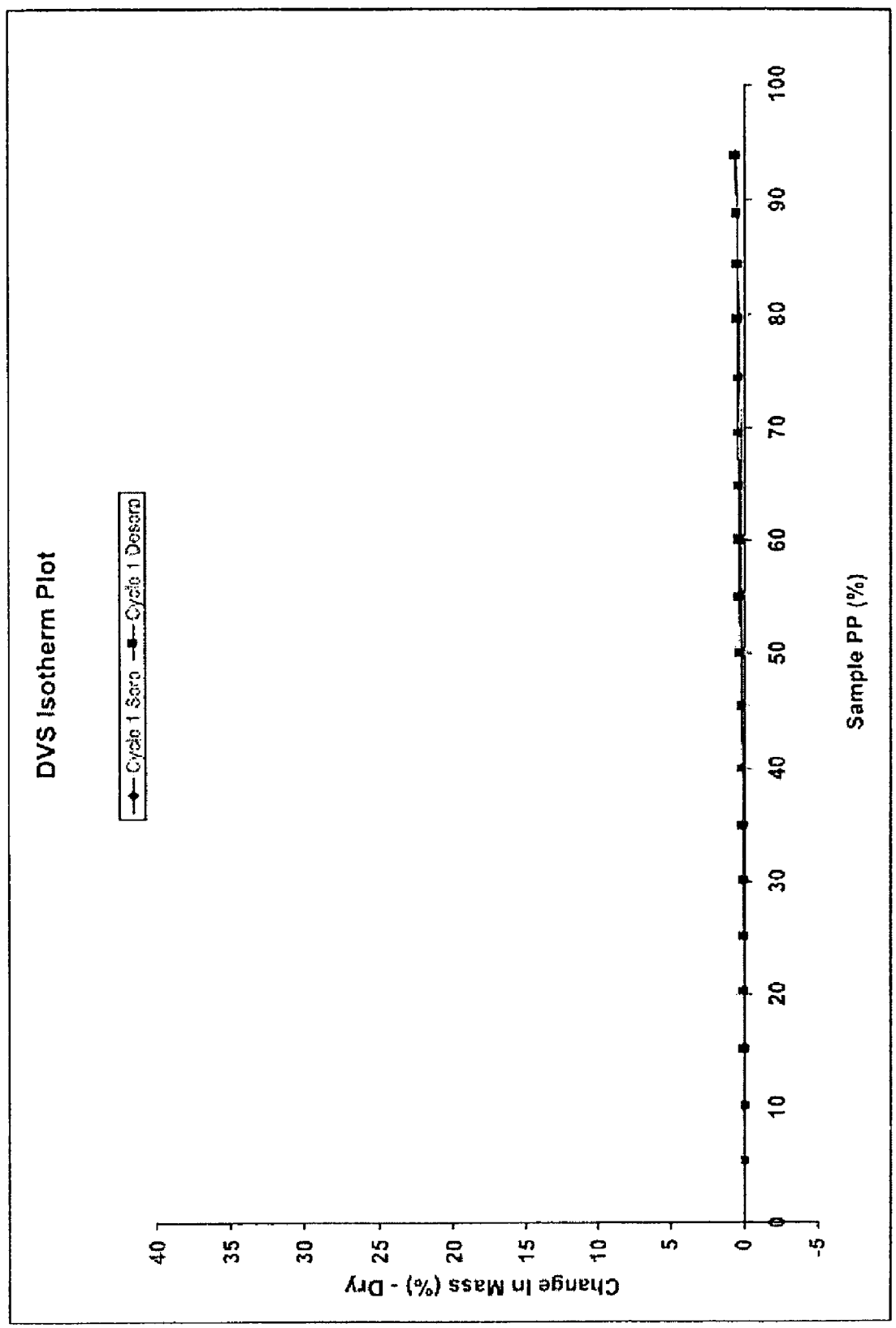
FIG. 2 shows an isothermal curve of water absorption and desorption in the compound of Example 1.
Figure 3:
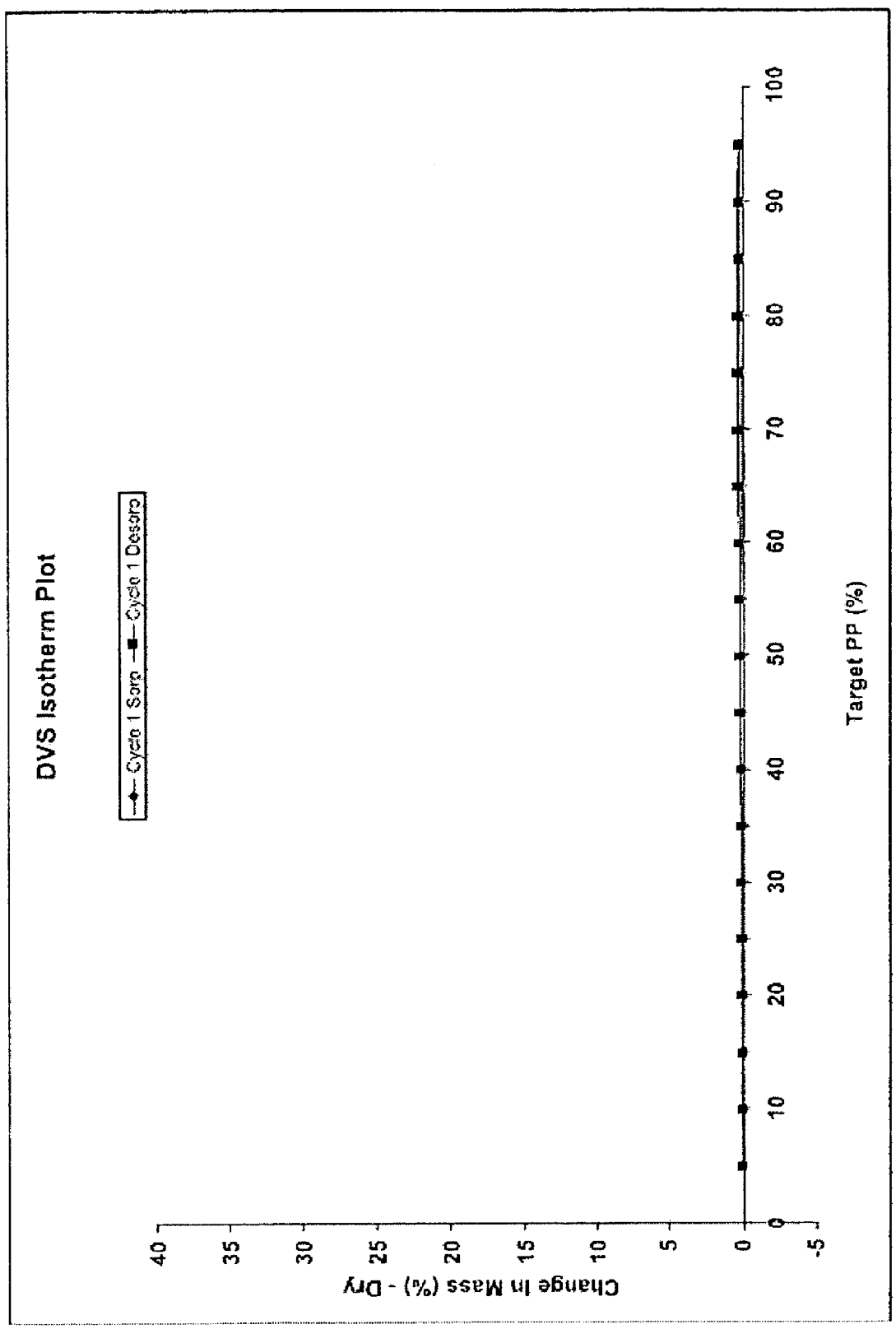
FIG. 3 shows an isothermal curve of water absorption and desorption in the compound of Example 2.
Figure 4:
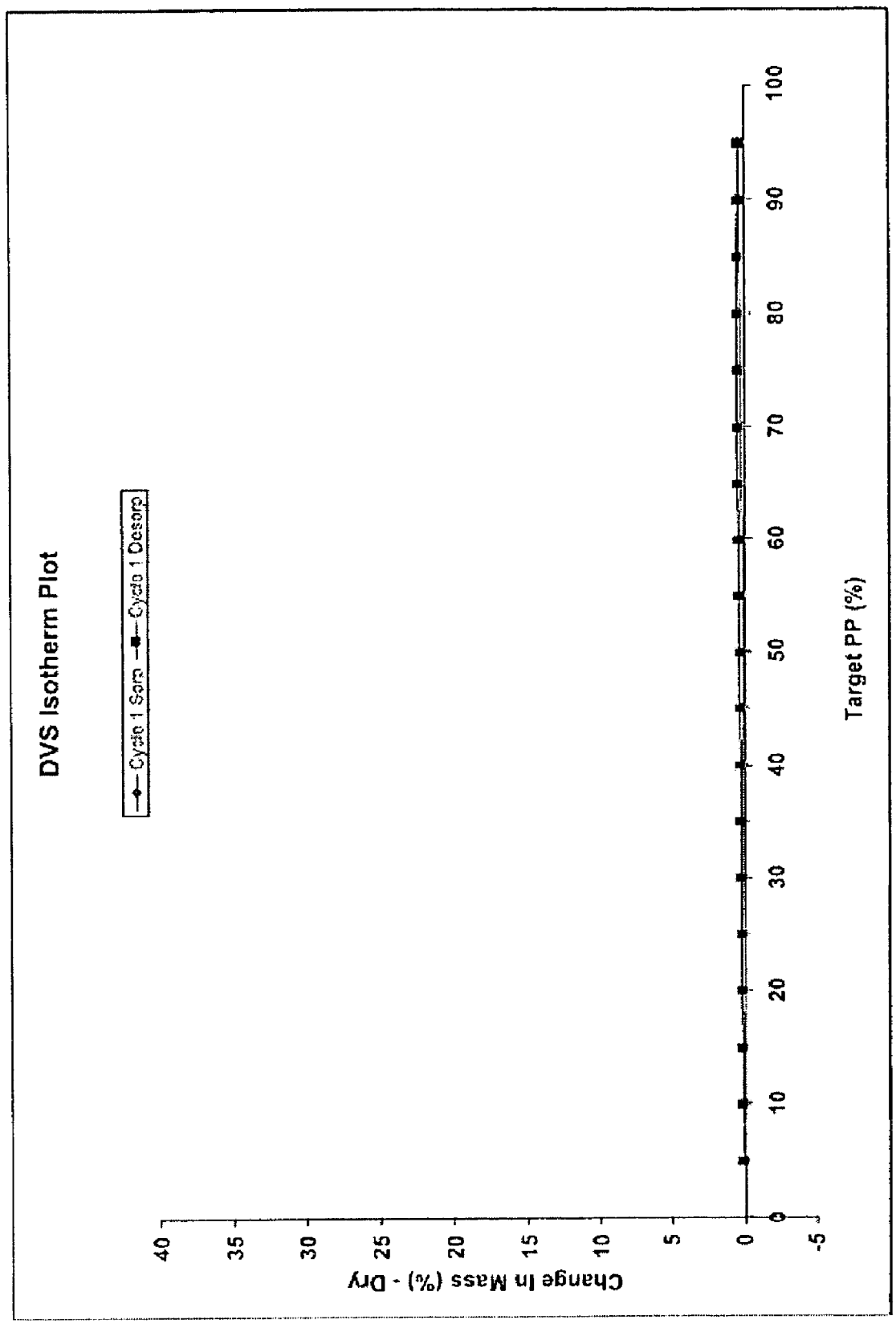
FIG. 4 shows an isothermal curve of water absorption and desorption in the compound of Example 3.
Figure 5:
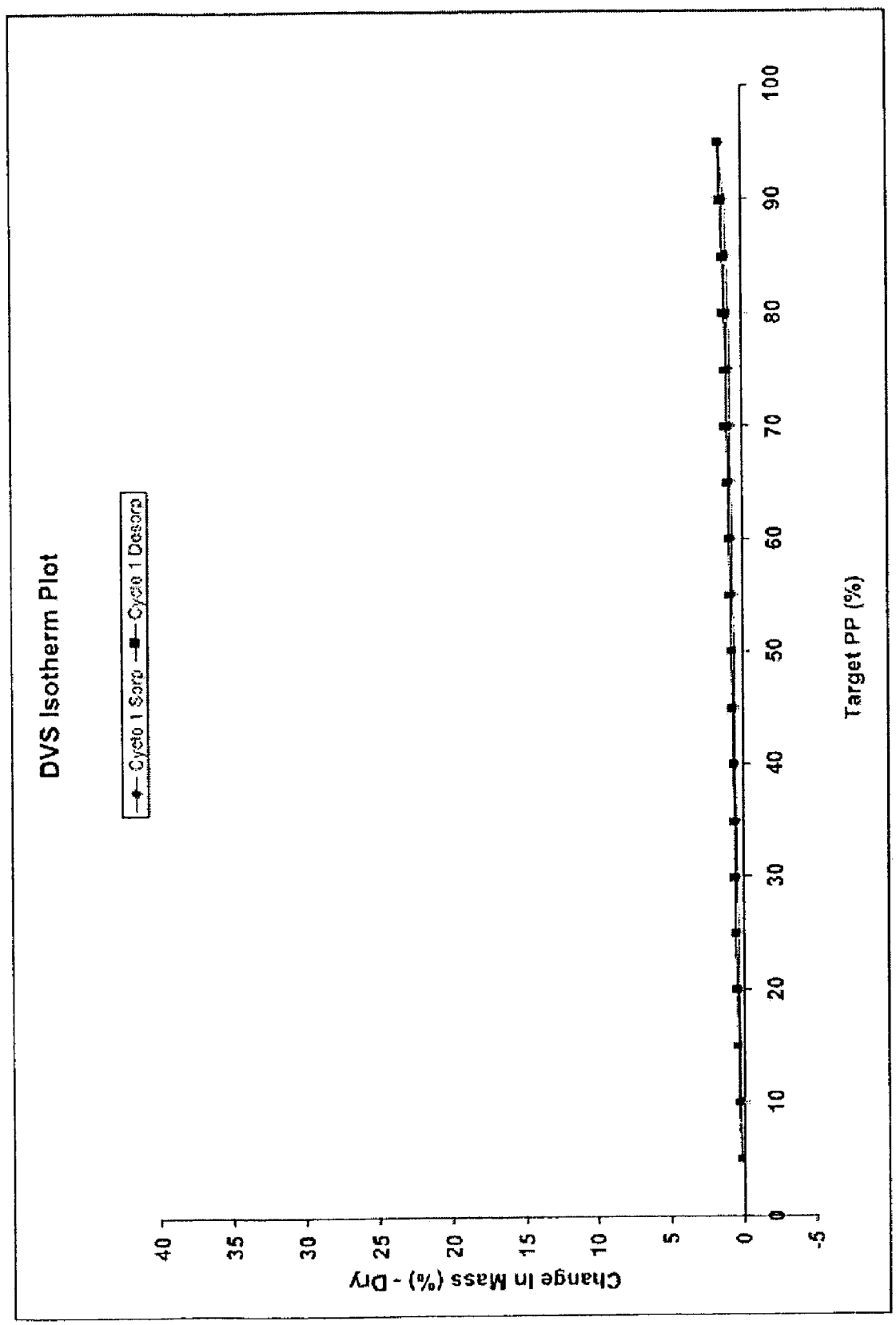
FIG. 5 shows an isothermal curve of water absorption and desorption in the compound of Example 4.
Figure 6:
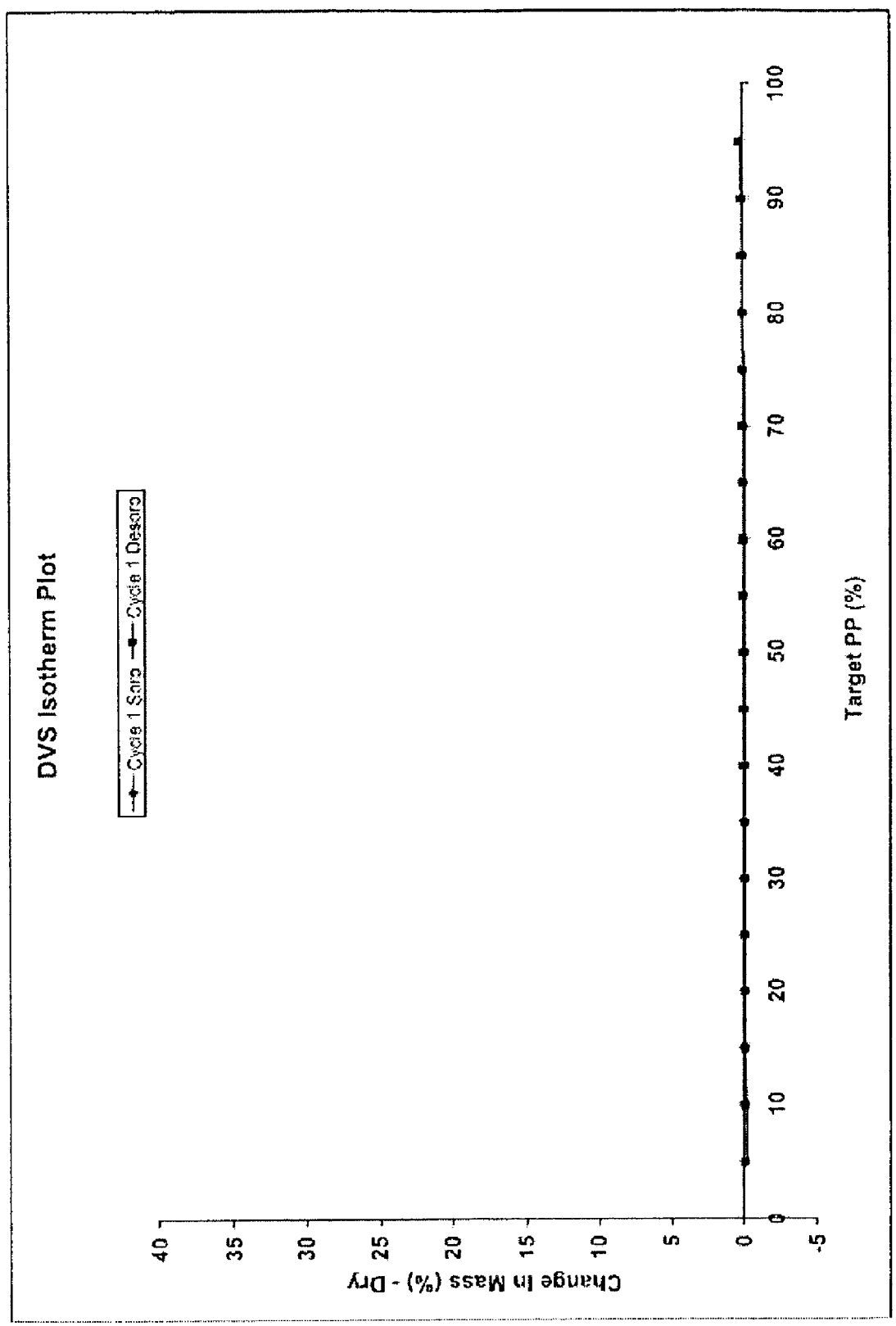
FIG. 6 shows an isothermal curve of water absorption and desorption in the compound of Example 5.
Figure 7:
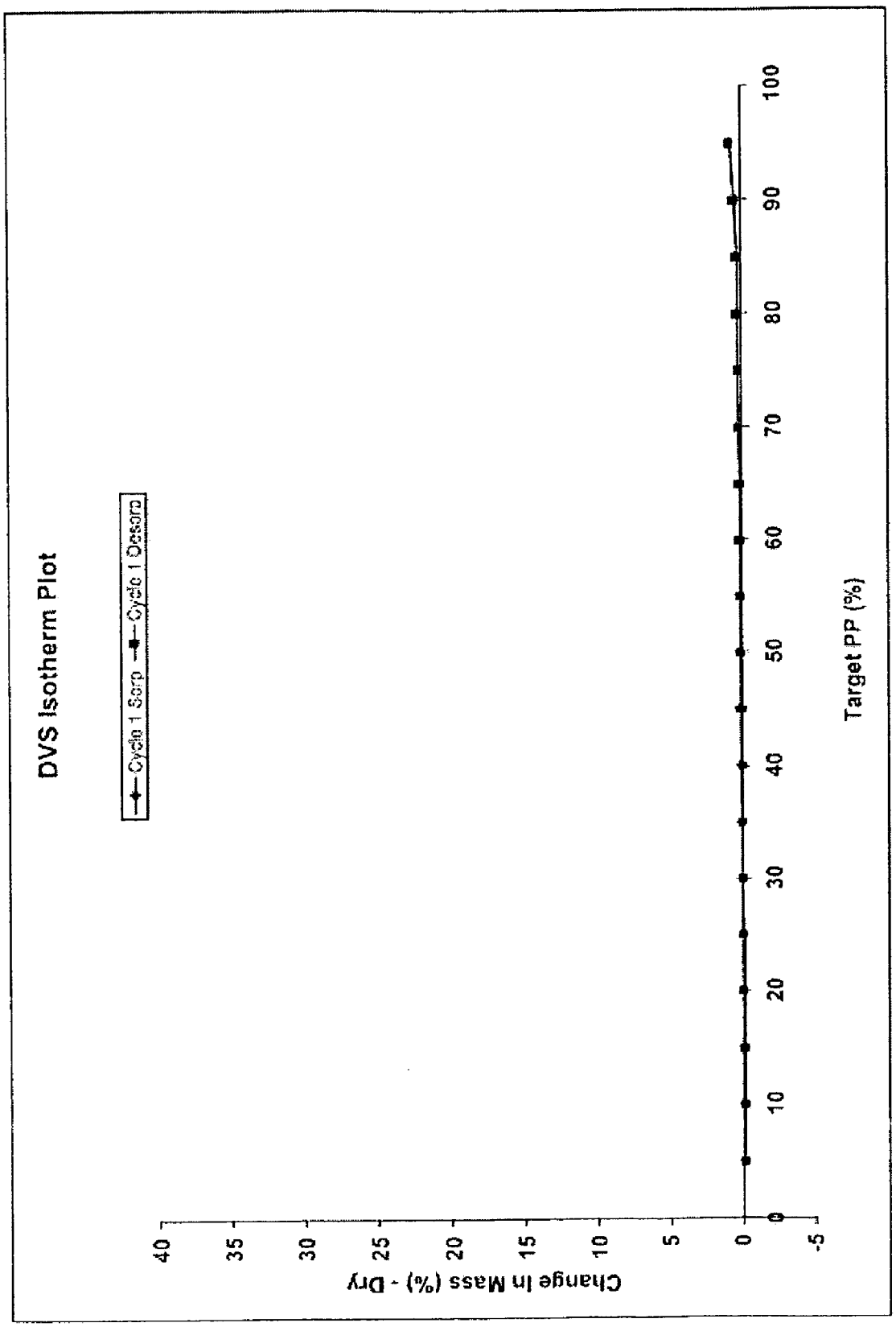
FIG. 7 shows an isothermal curve of water absorption and desorption in the compound of Example 5-1.
Figure 8:
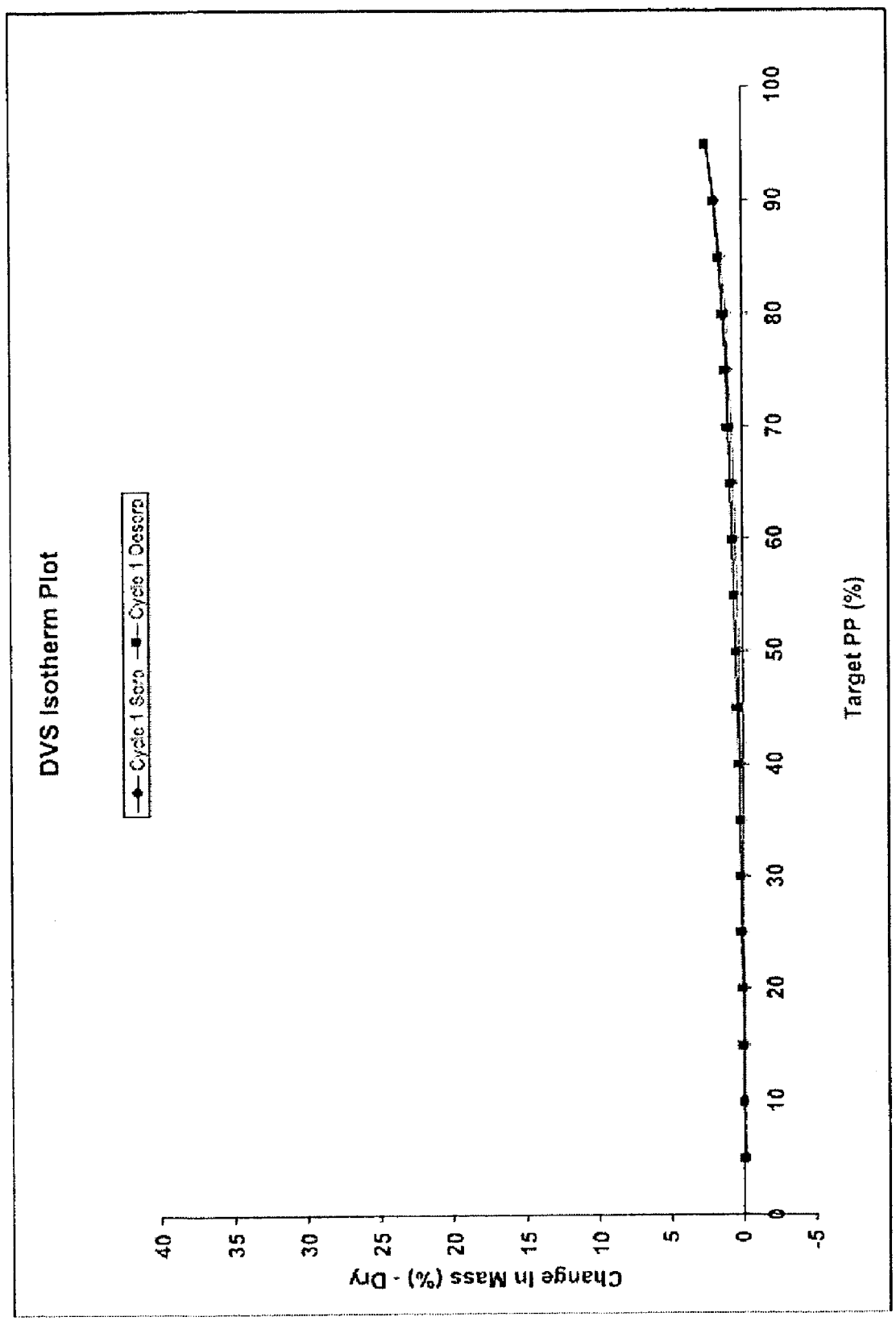
FIG. 8 shows an isothermal curve of water absorption and desorption in the compound of Example 6.
Figure 9:
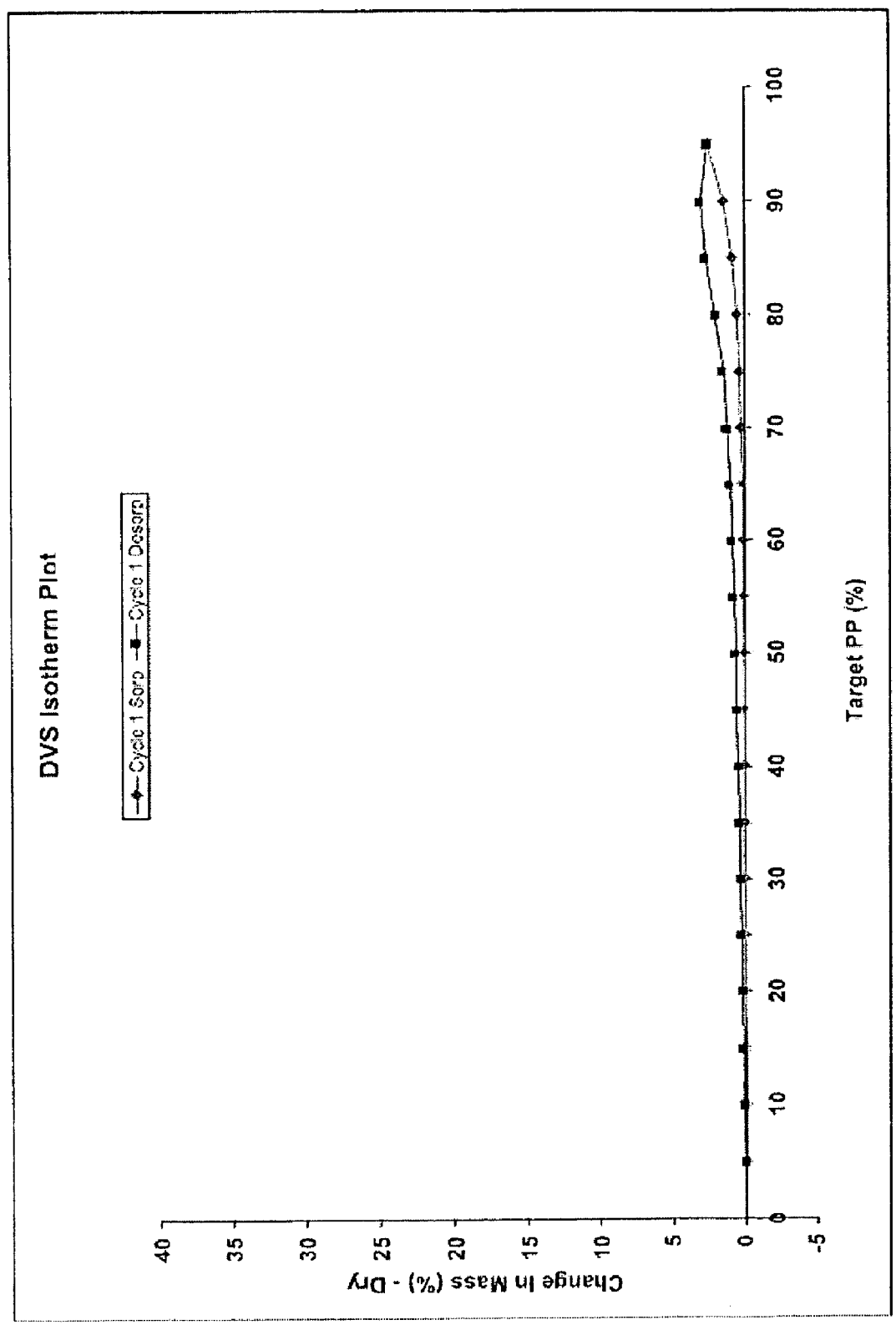
FIG. 9 shows an isothermal curve of water absorption and desorption in the compound of Example 7.
Figure 10:
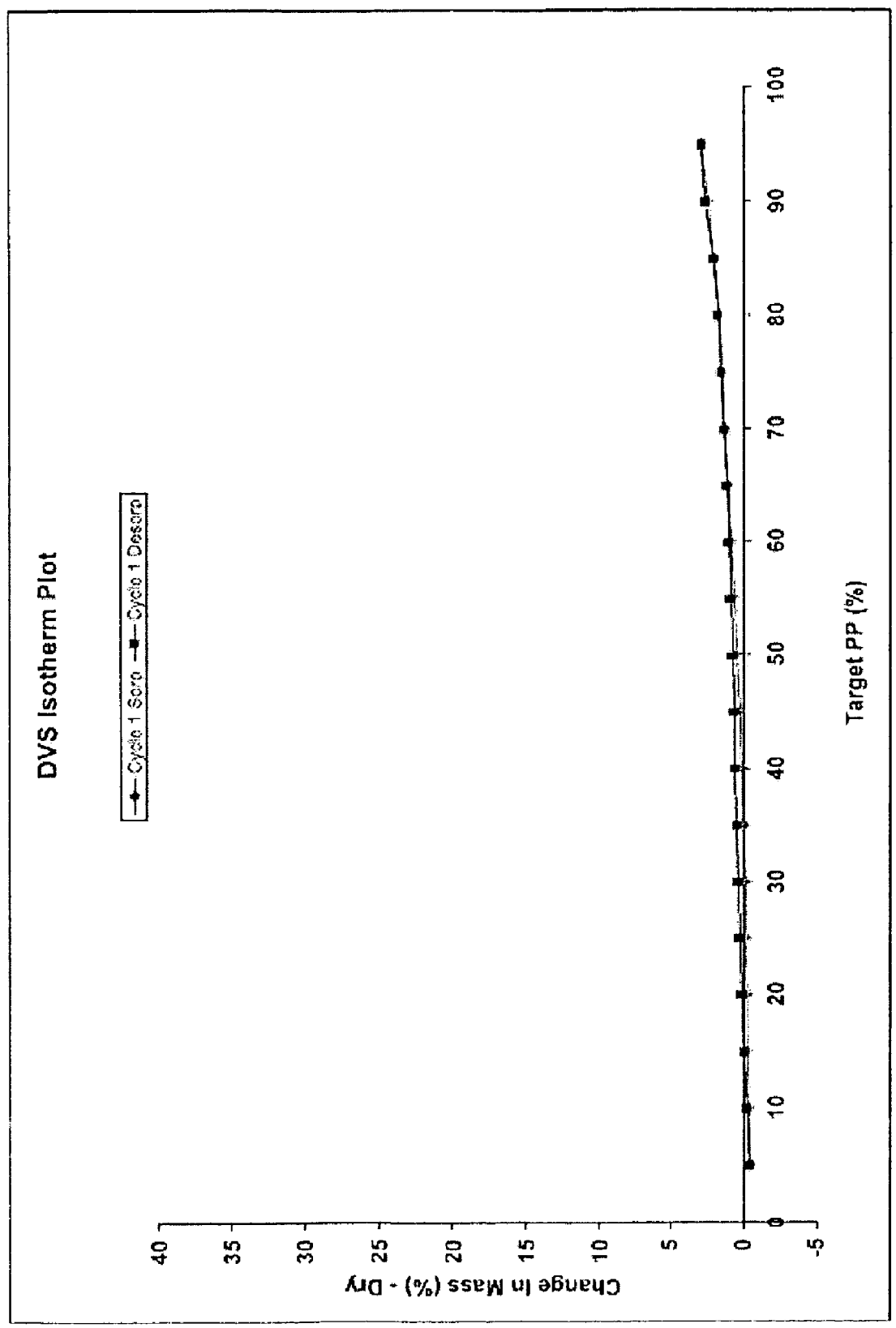
FIG. 10 shows an isothermal curve of water absorption and desorption in the compound of Example 8.
Figure 11:
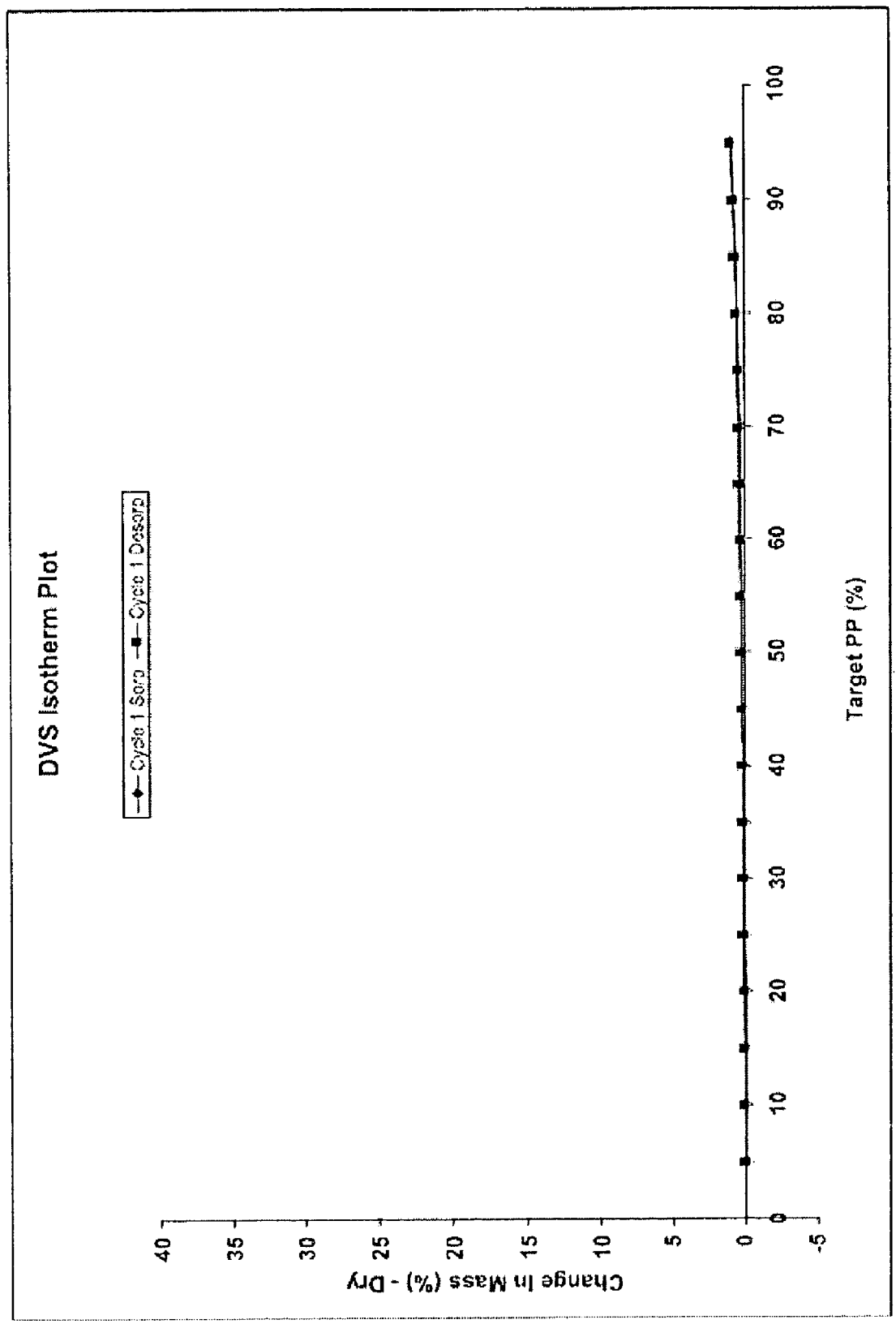
FIG. 11 shows an isothermal curve of water absorption and desorption in the compound of Example 9.
Figure 12:
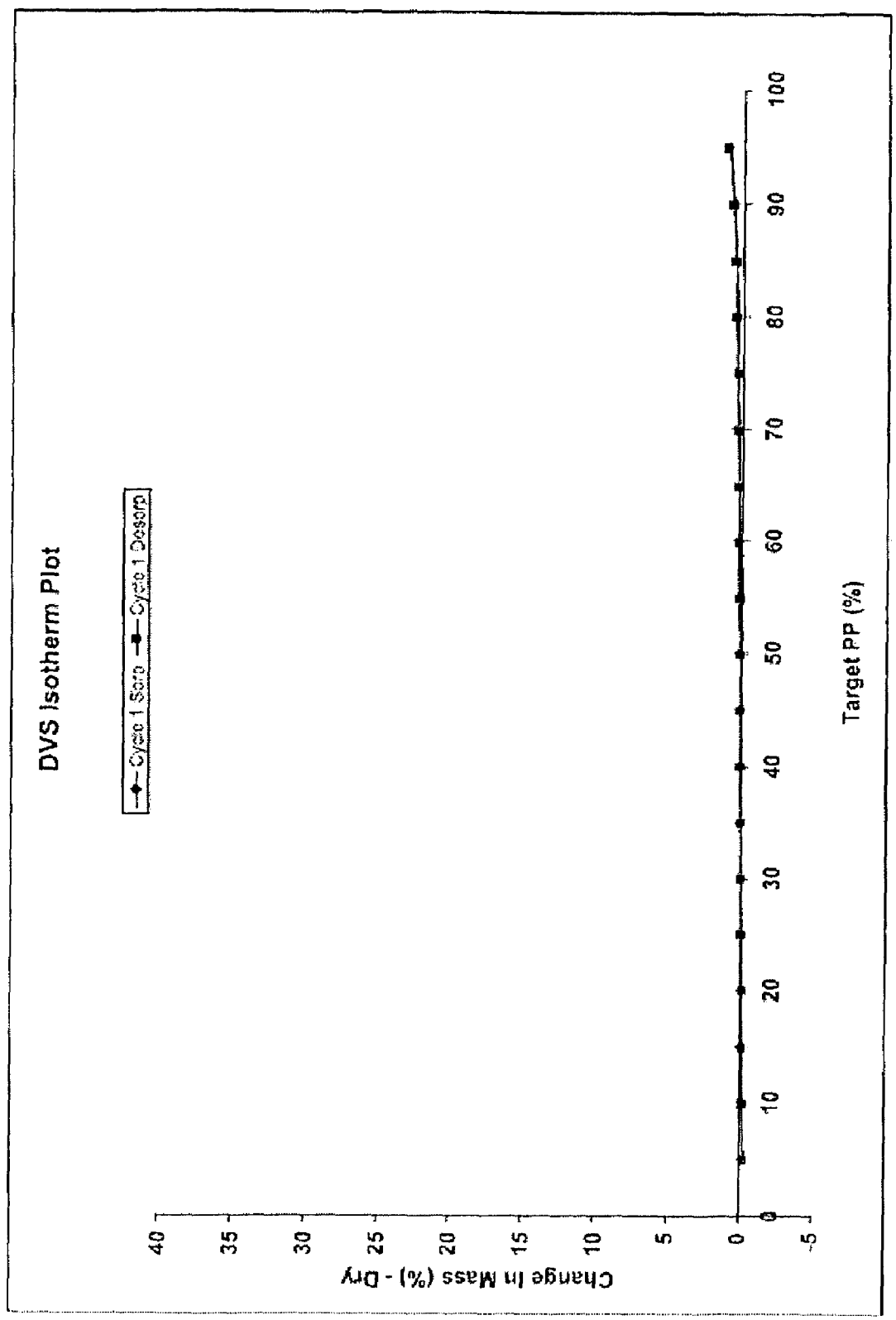
FIG. 12 shows an isothermal curve of water absorption and desorption in the compound of Example 10.
Figure 13:
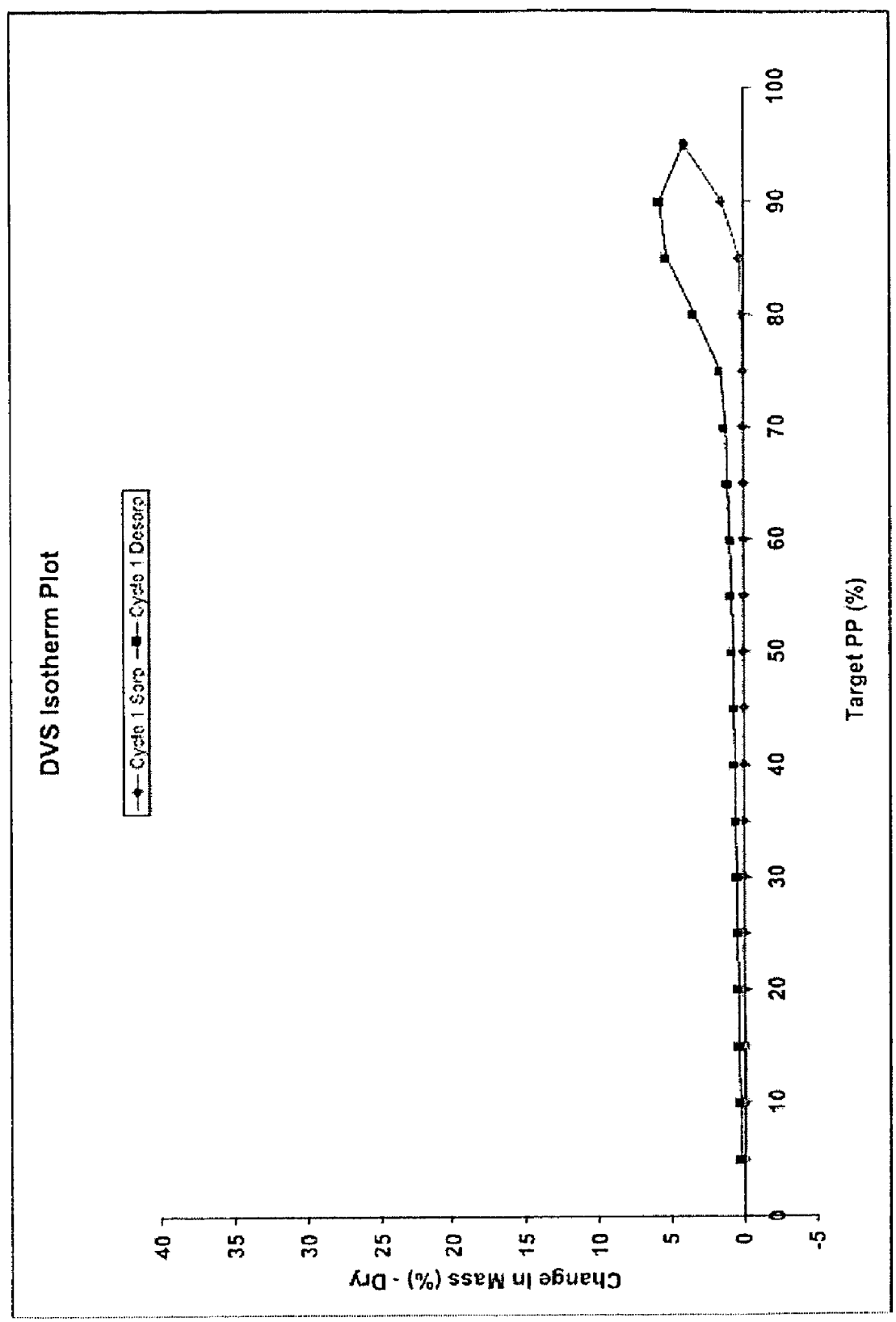
FIG. 13 shows an isothermal curve of water absorption and desorption in the compound of Example 11.
Figure 14:
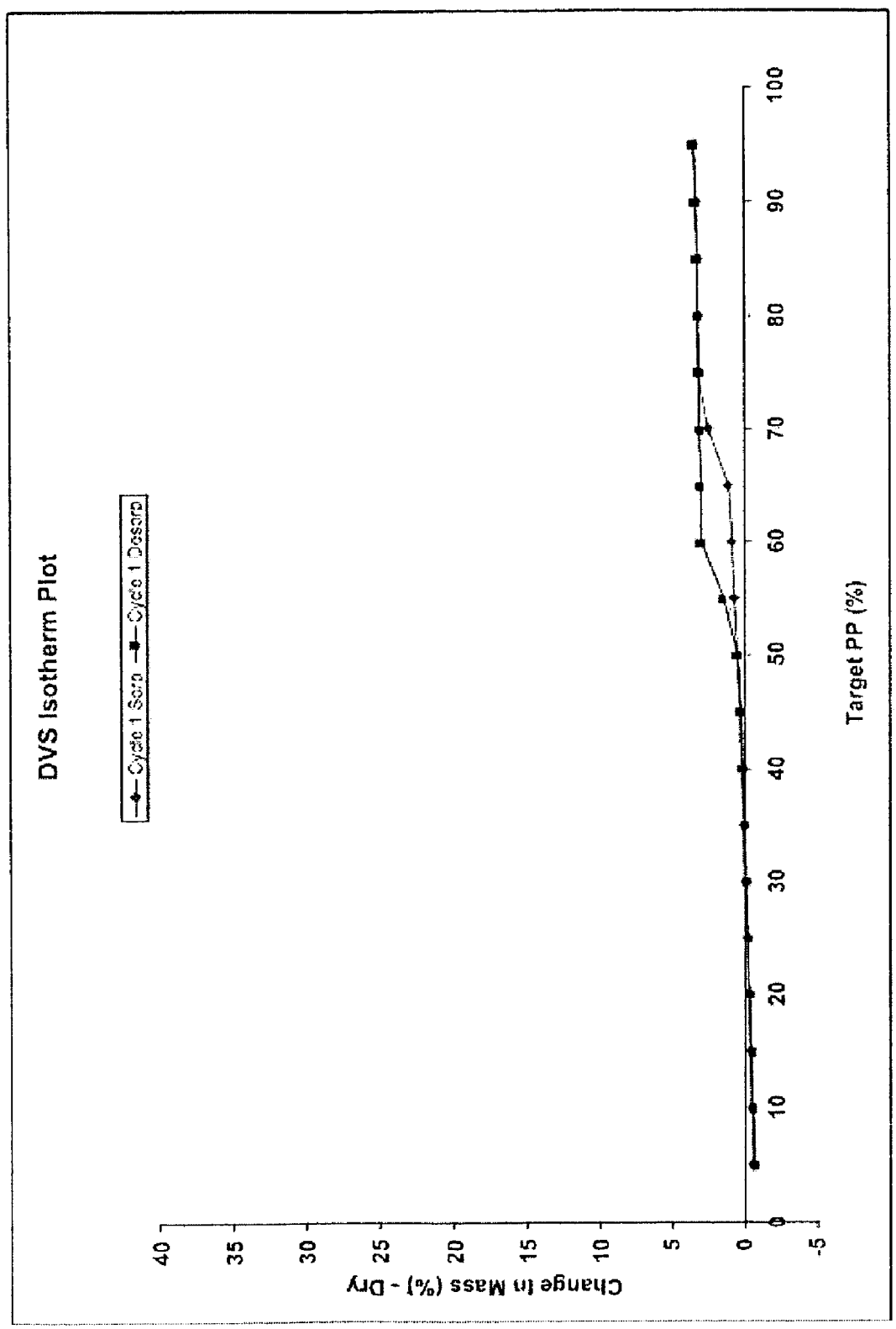
FIG. 14 shows an isothermal curve of water absorption and desorption in the compound of Example 12.
Figure 15:
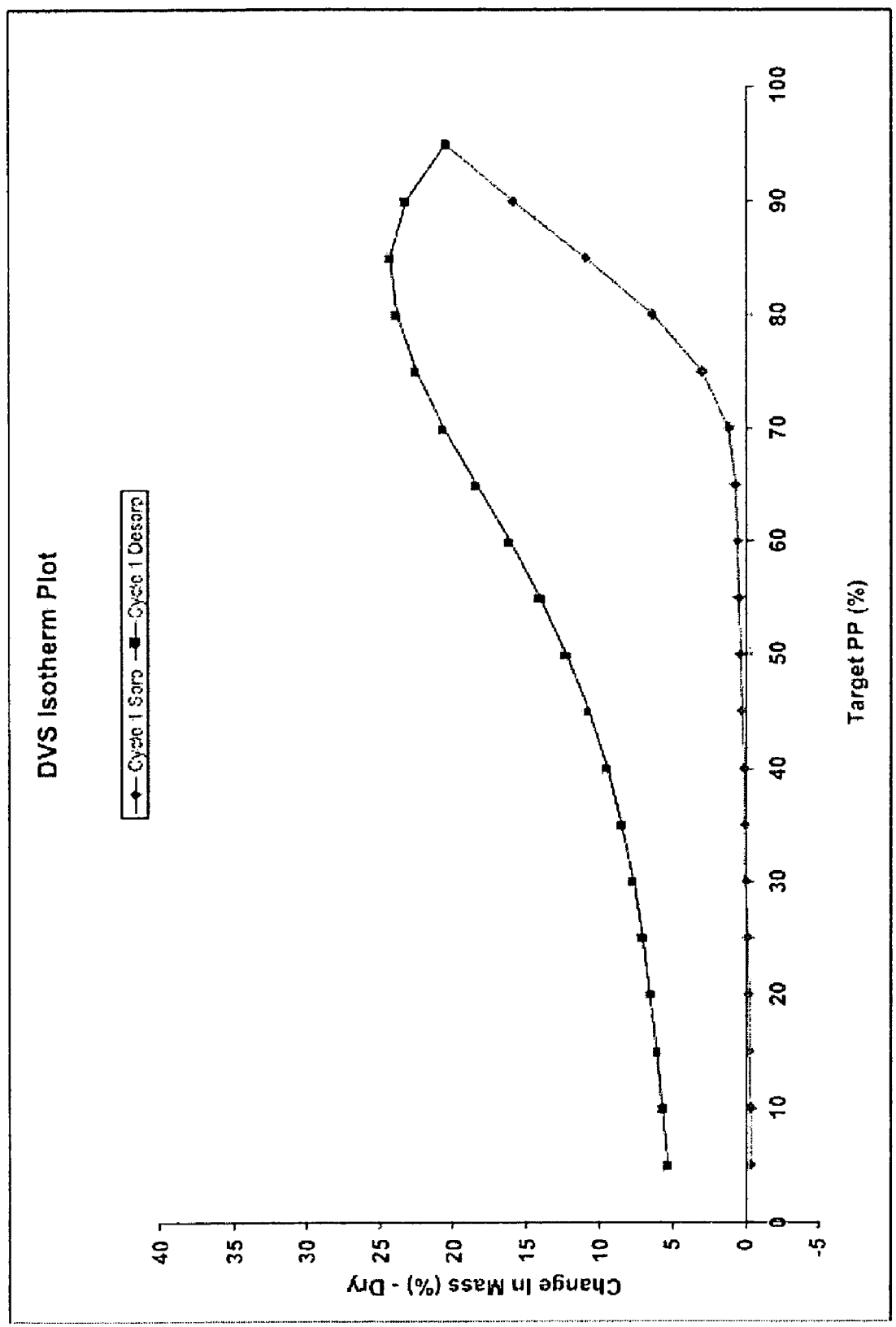
FIG. 15 shows an isothermal curve of water absorption and desorption in the compound of Example 13.
Figure 16:
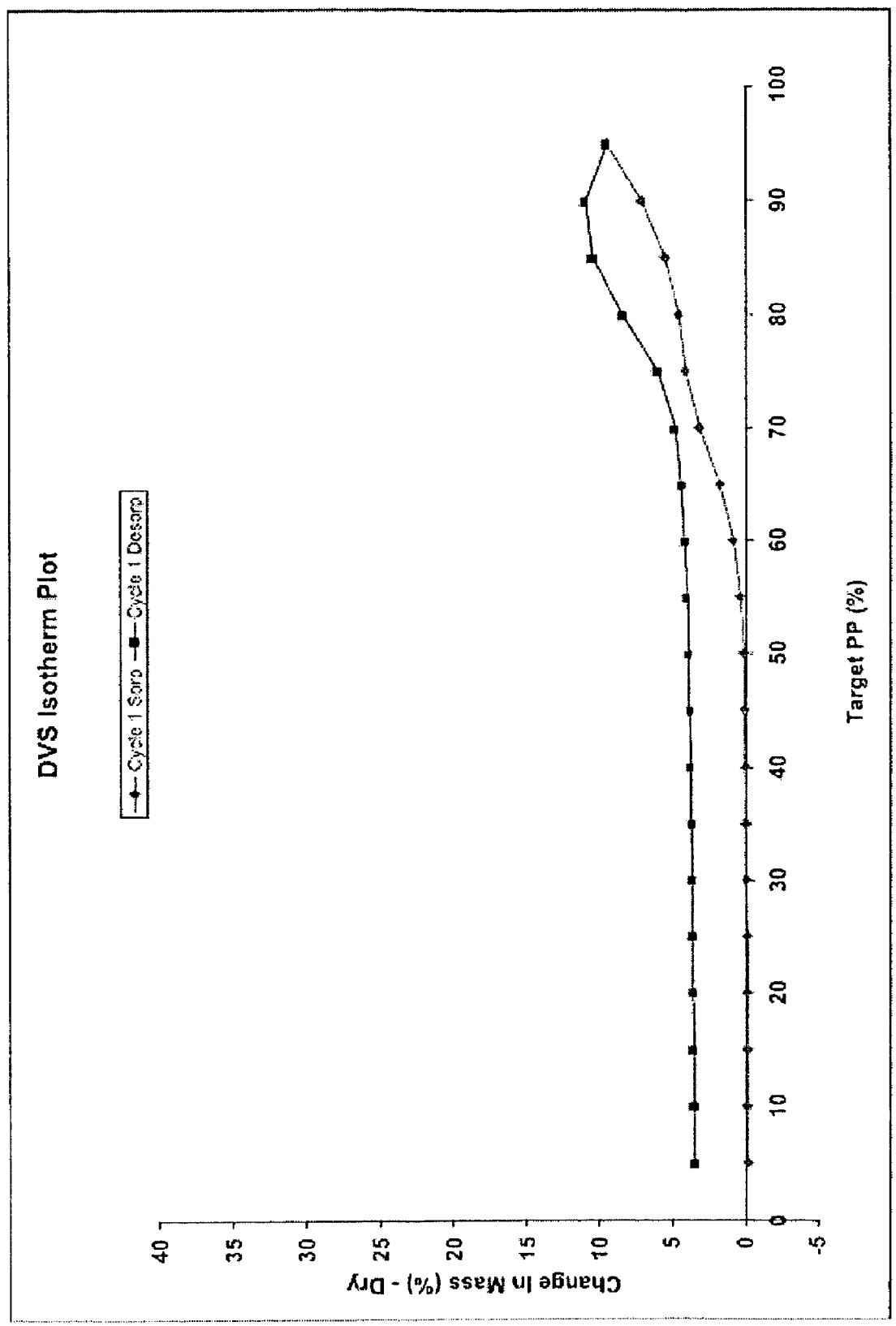
FIG. 16 shows an isothermal curve of water absorption and desorption in the compound of Example 14.

The acid addition salts of Compound A of the invention show a stability to a sufficient degree for use in pharmaceutical preparations or their drug substaces, have no hygroscopicity that affects the use as drugs or their drug substances, and are expected to be chemically stable or stable during storage. Therefore, all of the acid addition salts of the invention are preferred as drugs or their drug substances, particularly as drug substances for solid preparations.

(Manufacturing Method)

The acid addition salts of Compound A of the invention can be produced according to the following manufacturing method.

That is, a solvent is added to a free base of Compound A at a ratio of 1 mL/g–100 mL/g to Compound A, and then an acid used in formation of the salt or a solution containing the acid is added thereto in the range of 0.5 to 2.0 equivalents to Compound A at room temperature. When an insoluble material exists, the same solvent or a different solvent is added, or the mixture is heated for dissolving the insoluble material to give a solution, which is left with stirring or on standing at room temperature or under cooling. When an insoluble material is still remaining in spite of addition of solvent or heating, the mixture may be filtered to remove it before crystallization of the salt. Thus, the resulting crystals are collected by filtration and washed with a suitable solvent to give the objective acid addition salt of Compound A. In this operation for cooling to room temperature, it is sometimes effective to cool the mixture more gradually or rapidly rather than merely standing for cooling, in order to obtain better crystals.

The solvent/solvents which can be used in the above-mentioned salt formation include water, acetic acid, acetone, anisole, 1-butanol, 2-butanol, n-butyl acetate, t-butyl methyl ether, cumene, dimethylsulfoxide, ethanol (EtOH), ethyl acetate (EtOAc), diethyl ether, ethyl formate, formic acid, heptane, isobutyl acetate, isopropyl acetate (iPrOAc), methyl acetate, 3-methyl-1-butanol, methyl ethyl ketone (2-butanone), methyl isobutyl ketone, 2-methyl-1-propanol, pentane, 1-pentanol, 1-propanol, 2-propanol (2-PrOH), propyl acetate, acetonitrile, chlorobenzene, chloroform, cyclohexane, 1,2-dichloroethene, dichloromethane, 1,2-dimethoxyethane, DMF, DMA, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, THF, tetraline, toluene, 1,1,2-trichloroethene, xylene, benzene, carbon tetrachloride, 1,2-dichloroethane, 1,1-dichloroethene, 1,1,1-trichloroethane, diisopropyl ether, and the like.

Thus resulting crystals may be recrystallized in a conventional manner as employed by a person skilled in the art to give much more pure crystals.

A free base of Compound A which is a starting material in the above-mentioned manufacturing method may be produced according to the method as described in the above Patent document 1, i.e., European Patent No. 0 801 067, or its corresponding or similar method, or a method obviously employed by a person skilled in the art.

The acid addition salts of Compound A of the invention can be used as drug substances in production of pharmaceutical preparations by combining one or more of the acid addition salts of Compound A of the invention with conventional pharmaceutical carriers or diluents employed in this field. The pharmaceutical preparations may be produced by a method usually employed in this field.

The pharmaceutical preparations containing the acid addition salts of Compound A of the invention include orally administrable preparations such as tablets, pills, capsules, granules, powders, liquids and solutions, and the like; or parenteral preparations such as intraarticular, intravenous, or intramuscular injections, suppositories, percutaneous liquid preparations, ointments, transdermal stickers, transmucosal liquid preparations, transmucosal stickers, inhalations, and the like. Particularly, the oral preparations containing as a drug substance an acid addition salt of Compound A, such as tablets, pills, capsules, granules and powders, are advantageous as stable solid preparations.

In the solid compositions for use in oral administration, one or more of the active ingredients may be mixed with at least one inert diluent, for example, lactose, mannitol, glucose, hydroxypropylcellulose, fine crystal cellulose, starch, polyvinylpyrrolidone, magnesium metasilicate aluminate, and the like. The compositions may contain additives other than diluents in a conventional manner, for example, lubricants such as magnesium stearate, disintegrating agents such as fibrous calcium glycolate, stabilizers, or solubilizing agents. The tablets or pills if required may be coated with sugar-coating or a gastric or enteric coating film, such as sucrose, gelatin, hydroxypropylcellulose, hydroxypropylmethylcellulose, and the like.

The liquid compositions for oral administration include pharmaceutically acceptable emulsions, solutions, suspensions, syrups, elixirs, and the like, which contain conventionally used diluents, for example, purified water or ethanol. In addition to inert diluents, the compositions may further contain auxiliary agents such as wetting agent or suspending agent, sweetener, flavor, perfume, or preservative.

The injections for parenteral administration include sterile aqueous or non-aqueous solutions, suspensions and emulsions. The aqueous solutions and suspensions include, for example, distilled water for injection and physiological saline. The non-aqueous solutions and suspensions include, for example, propylene glycol, polyethylene glycol, vegetable oils such as olive oil, alcohols such as EtOH, polysorbate 80, and the like. Such a composition may further contain a preservative, wetting agent, emulsifying agent, dispersant, stabilizer, solubilizing agent, and the like. These may be sterilized for example by filtration through a bacterium-impermeable filter, blending with a bactericide, or irradiation. Alternatively, these may be made into a sterile solid composition, which is dissolved in sterile water or sterile solvent for injection just before use.

Since the pharmaceutical compositions of the present invention comprise one or more of the acid addition salts of Compound A of the invention, which are muscarinic $M_3$ receptor antagonists, as the active ingredient, the pharmaceutical compositions may be used for the therapy or prophylaxis of a variety of diseases to which muscarinic $M_3$ receptors contribute or may be 3 mployed in diagnostic procedures. That is, the pharmaceutical compositions of the invention, specifically, are useful as regimen in the treatment of, for example, urinary urgency, frequency/pollakisuria, urinary incontinence, nocturnal enuresis or hyperreflexic bladder caused by urinary diseases, such as overactive bladder, unstable bladder, neurogenic bladder, cystitis, etc.; in the therapy or prophylaxis of bladder spasm caused by surgery or catheters; in the treatment of respiratory diseases such as chronic obstructive pulmonary disease, chronic bronchitis, asthma and rhinitis; in the treatment of digestive diseases, such as irritable bowel syndrome; as the relaxant used for examination of the digestive tract; as an agent to ameliorate myopia or to promote mydriasis; or as an agent to treat or prevent hyperhidrosis.

EXAMPLES

The invention will be explained specifically by the following examples which are not intended as a limitation thereof and are not intended to restrict the scope of the invention.

The thermal analysis and powder X-ray diffractometry were performed according to the following methods.

(1) Thermal Analysis (Differential Scanning Calorimetry: DSC)

A sample (about 3 mg) was placed in a purpose-made aluminum pan. The change of heat generated between the sample and a reference (empty aluminum pan) was continuously measured and recorded under a nitrogen atmosphere (50 ml/min) in the temperature range of room temperature to 300° C. at a rate of 10° C./min of ascending programmed temperature. The apparatus including data processing was operated according to the method and procedure directed in each device. (Apparatus: Hi-Res DSC 2910, made by TA Instrument)

(Thermogravimetric Apparatus: TGA)

A sample (about 3 mg) was placed in a purpose-made platinum pan, and the sample weight was continuously measured and recorded under a nitrogen atmosphere (100 ml/min) in the temperature range of room temperature to 300° C. at a rate of 10° C./min of ascending programmed temperature. The apparatus including data processing was operated according to the method and procedure directed in each device. (Apparatus: Hi-Res TGA 2950, made by TA Instrument)

(2) Powder X-Ray Diffractometry

A sample (about 10 mg) was placed in a purpose-made sample holder (5 mm wide, 18 mm long, 0.2 mm height), and the X-ray diffraction pattern was carried out and the data recorded according to the following condition. The apparatus including data processing was operated according to the method and procedure directed in each device. (Apparatus: MXP18TAHF22, made by MAC Science (Bruker at present))

(Condition)

X-ray radiation source: Cu; wavelength: 1.54056 angstrom; range of measurement: 3.00–40.00°; sampling interval: 0.02°; scanning rate: 3.00°/min; tube voltage: 40 kV; tube current: 200 mA; divergence slit: 1.00°; scattering slit: 1.00°; receiving slit: 0.15 mm The values obtained from each spectrum sometimes in some degree depend on the direction of crystal growth, particle size, and the condition of measurement. These values should not be assessed strictly, accordingly.

Reference Example 1

Preparation of Compound A in a Free State

The title compound was prepared according to the method as described in European Patent No. 0 801 067.

Reference Example 2

Preparation of Compound A Hydrochloride as a Reference Compound

The title compound was prepared according to the method as described in European Patent No. 0 801 067.

Example 1

Preparation of Compound A (−)-(2S,3S)-tartrate

To a solution of Compound A free base (26.0 g) in 260 mL of EtOH was added 10.8 g of (−)-(2S,3S)-tartaric acid, and the mixture was heated to be dissolved. After cooling to room temperature, the mixture was stirred for 20 hours. The resulting crystals were collected by filtration to give 30.6 g of white crystals. To a suspension of 1.00 g of the crystals in 10 mL of EtOH was added 0.4 mL of water, and the mixture was heated to give a solution. After cooling to room temperature, the mixture was stirred for 6 hours. The resulting crystals were collected by filtration to give 871 mg of the title compound as white crystals.

$^1$H-NMR(DMSO-d$_6$, 25.9° C.): 1.40–1.98 (4H, m), 2.00–2.25 (1H, m), 2.70–3.20 (7H, m), 3.33–3.53 (2H, m), 3.83–3.94 (1H, m), 3.99 (2H, s), 4.85 (1H, brs), 6.25 (1H, brs), 7.08–7.37 (9H, m).

Peak top temperature of endothermia in DSC: 194° C.

Figure 17:
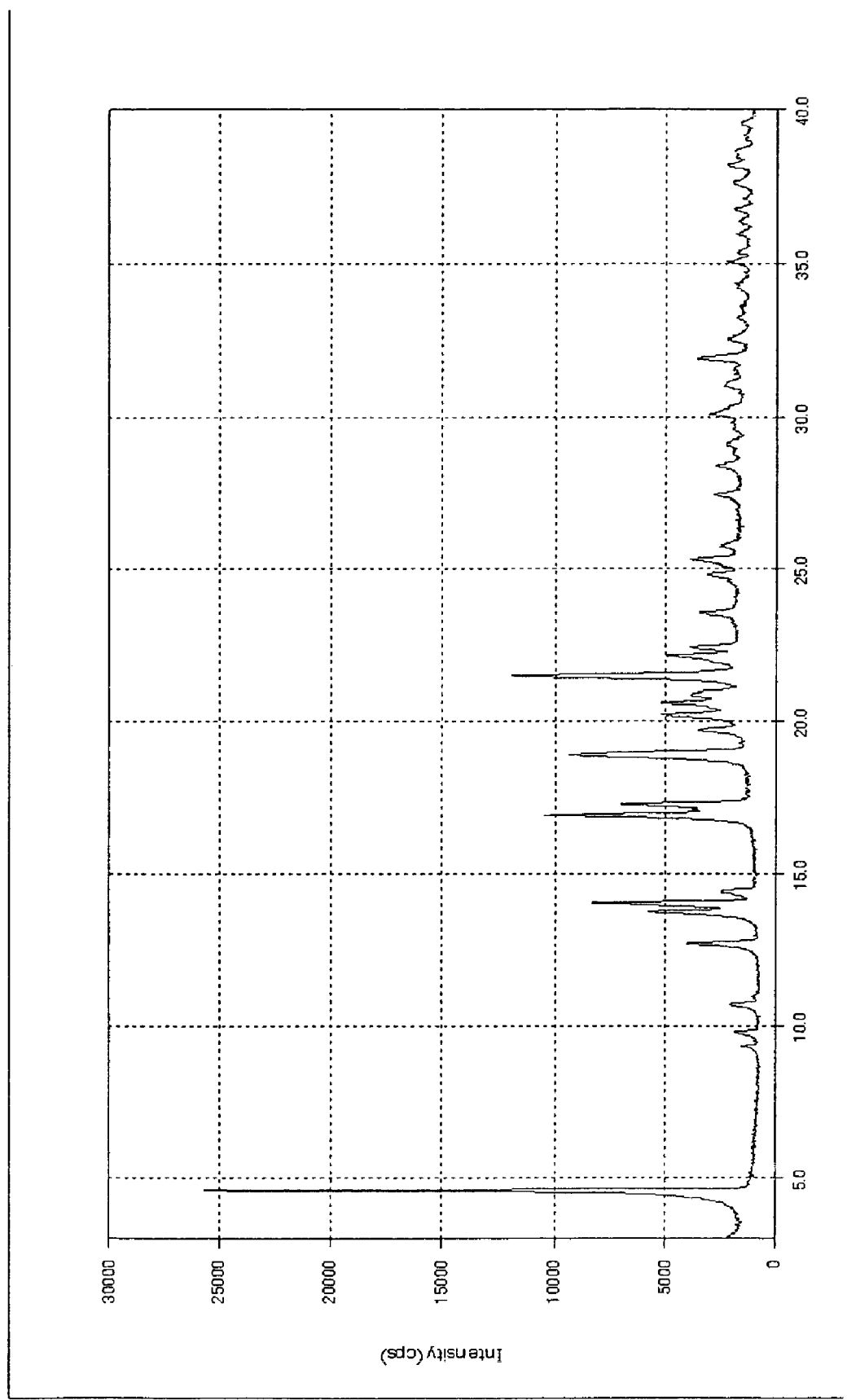
FIG. 17 shows a powder X-ray diffraction pattern of the compound of Example 1.

FIG. 17 shows a powder X-ray diffraction pattern of the compound in Example 1.

Example 2

Preparation of Compound A (+)-(2S,3S)-di-O-benzoyltartrate

To a solution of Compound A free base (180 mg) in 1.8 mL of EtOH was added 180 mg of (+)-(2S,3S)-di-O-benzoyltartaric acid, and the mixture was stirred at room temperature for 12 hours. The resulting crystals were collected by filtration, washed with EtOH and dried under reduced pressure to give 284 mg of the title compound as white crystals.

$^1$H-NMR(DMSO-d$_6$: 70° C.): 1.52–1.90 (4H, m), 2.16 (1H, brs), 2.76–3.16 (7H, m), 3.37–3.56 (2H, m), 3.89 (1H, dt, J=13.2, 5.4 Hz), 4.85–4.92 (1H, m), 5.68 (2H, s), 6.23 (1H, s), 7.11–7.33 (9H, m), 7.43–7.55 (4H, m), 7.57–7.63 (2H, m), 7.90–7.96 (4H, m).

Peak top temperature of endothermia in DSC: 159° C.

Figure 18:
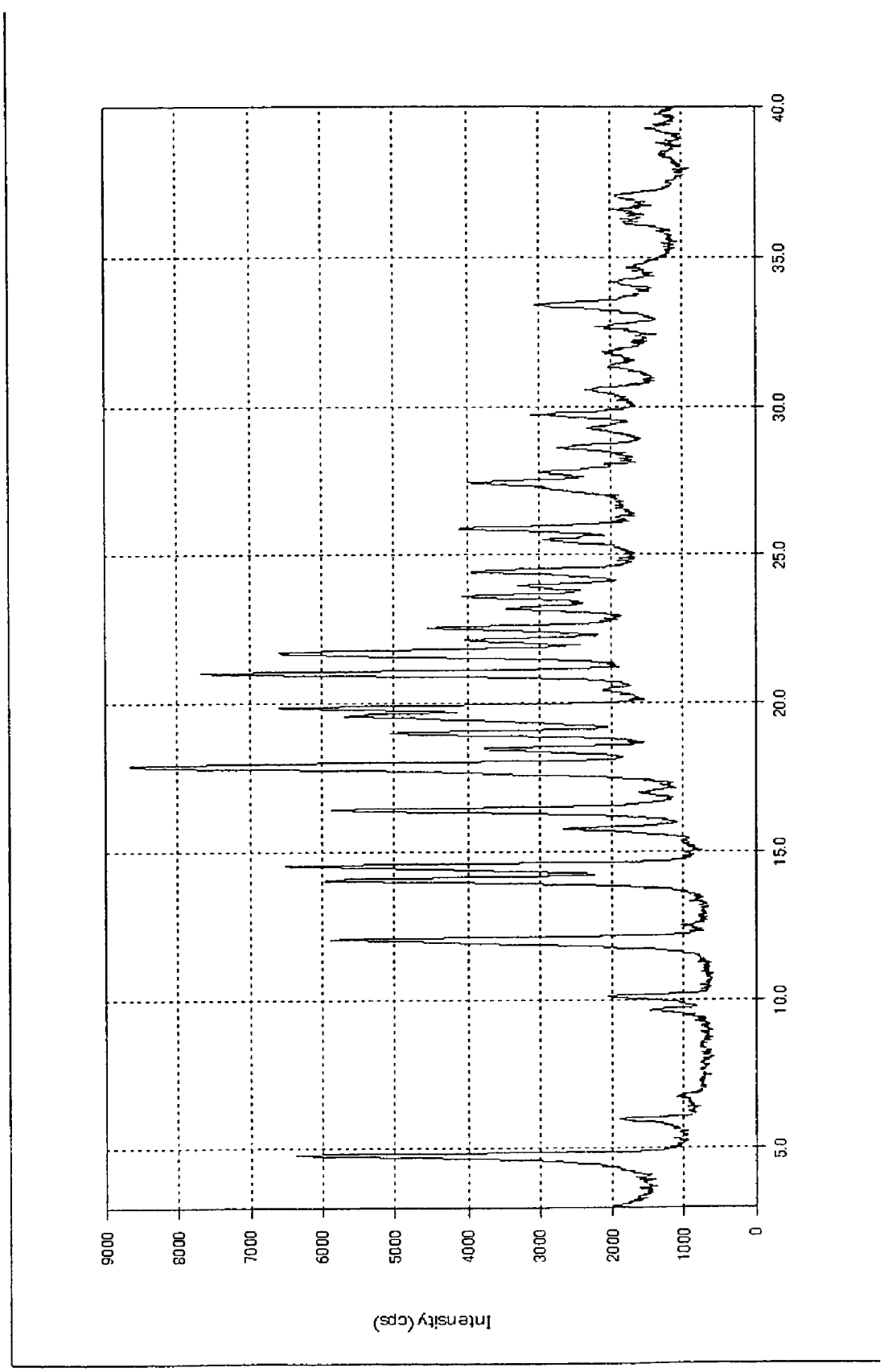
FIG. 18 shows a powder X-ray diffraction pattern of the compound of Example 2.

FIG. 18 shows a powder X-ray diffraction pattern of the compound in Example 2.

Example 3

Preparation of Compound A (+)-(2S,3S)-di-O-(4methylbenzoyl)tartrate

To a solution of Compound A free base (1.00 g) in 20 mL of ETOH was added 1.12 g of (+)-(2S,3S)-di-O-(4-methylbenzoyl)tartaric acid, and the mixture was stirred at room temperature for 22 hours. The resulting precipitates were collected by filtration to give 1.60 g of the title compound as white crystals.

$^1$H-NMR(DMSO-d$_6$: 70° C.): 1.53–1.88 (4H, m), 2.15 (1H, brs), 2.32–2.38 (6H, m), 2.76–3.16 (7H, m), 3.42 (1H, ddd, J=13.6, 8.8, 5.2 Hz), 3.50 (1H, dd, J=14.4, 8.8 Hz), 3.90 (1H, dt, J=13.2, 5.2 Hz), 4.88 (1H, dt, J=8.8, 4.4 Hz), 5.64 (2H, s), 6.23 (1H, s), 7.11–7.34 (13H, m), 7.77–7.84 (4H, m).

Peak top temperature of endothermia in DSC: 160° C.

Figure 19:
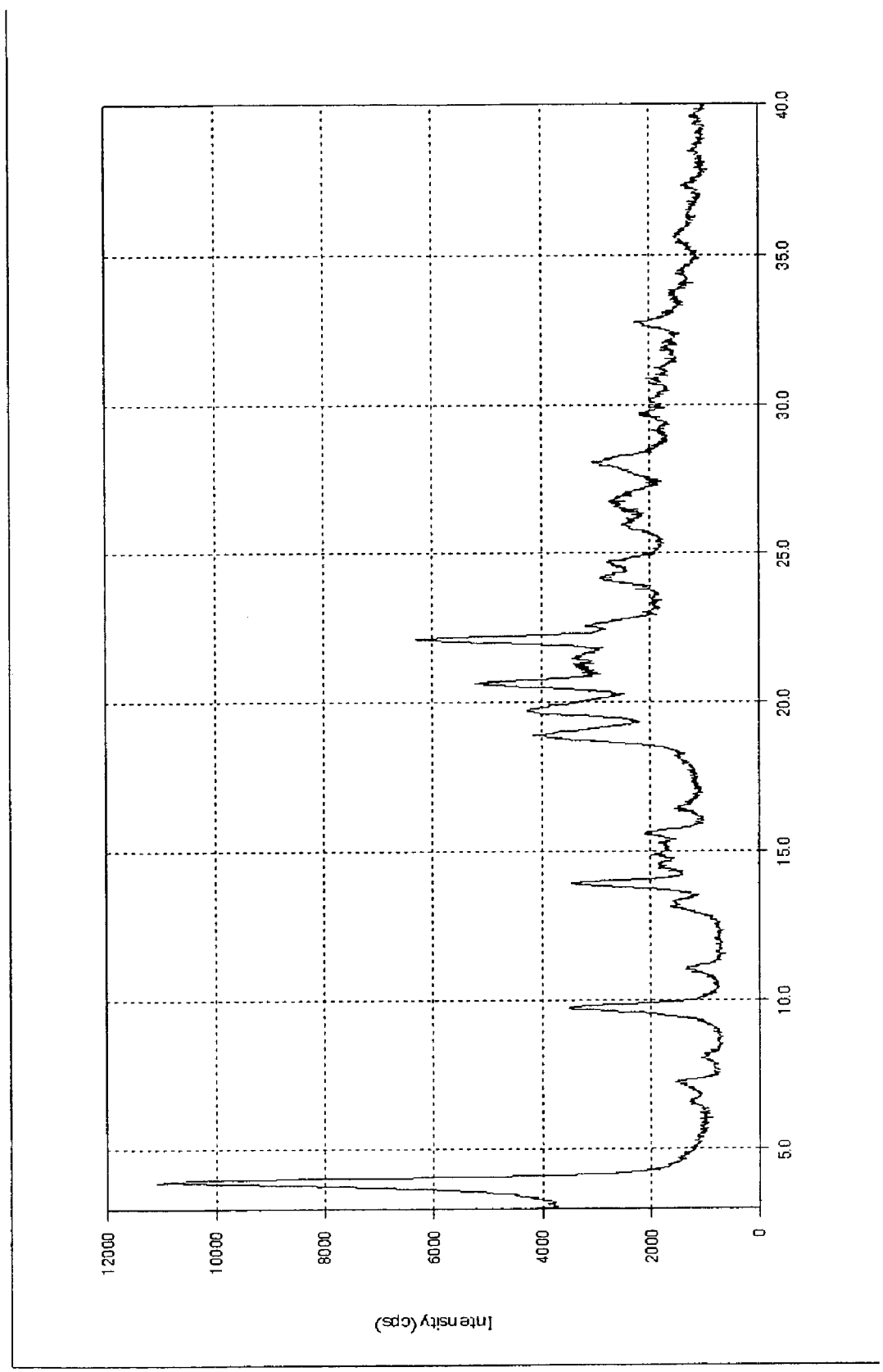
FIG. 19 shows a powder X-ray diffraction pattern of the compound of Example 3.

FIG. 19 shows a powder X-ray diffraction pattern of the compound in Example 3.

Example 4

Preparation of Compound A (−)-L-phenylalaninate

To a solution of Compound A free base (1.13 g) in 11.25 mL of EtOH were added 515 mg of (−)-L-phenylalanine and 4.5 mL of water, and the mixture was heated to be dissolved. The mixture was then stirred at room temperature for 10 hours. The resulting crystals were collected by filtration, washed with a mixture of water-EtOH and dried under reduced pressure to give 1.12 g of the title compound as white crystals.

$^1$H-NMR(DMSO-d$_6$: 70.0° C.): 1.20–1.36 (1H, m), 1.41–1.70 (3H, m), 1.86–1.95 (1H, m), 2.50–2.95 (8H, m), 3.03–3.17 (2H, m), 3.33–3.47 (2H, m), 3.84–3.95 (1H, m), 4.60–4.71 (1H, m), 6.23 (1H, s), 7.11–7.33 (14H, m).

Peak top temperature of endothermia in DSC: 118° C. and 235° C.

Figure 20:
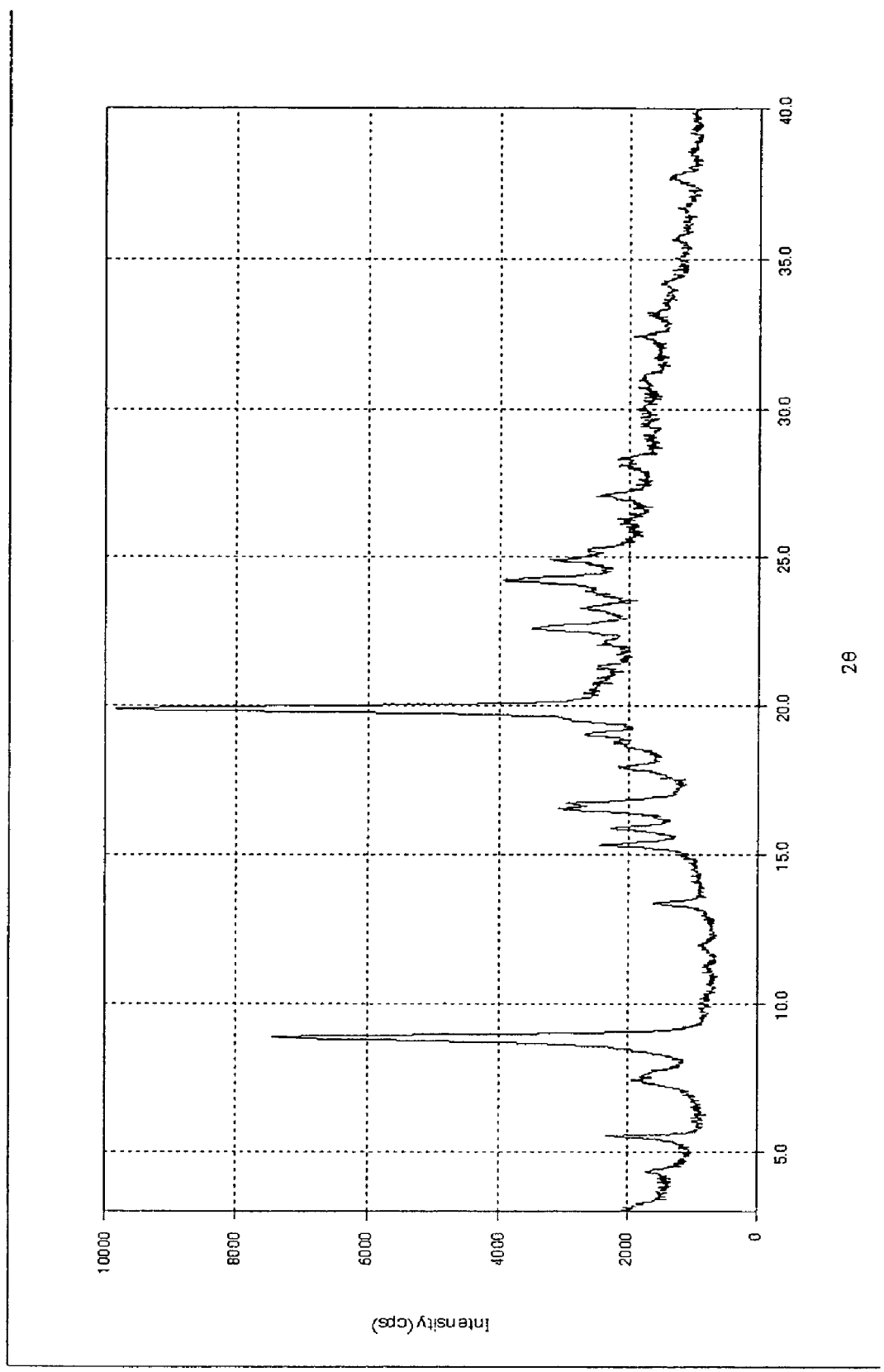
FIG. 20 shows a powder X-ray diffraction pattern of the compound of Example 4.

FIG. 20 shows a powder X-ray diffraction pattern of the compound in Example 4.

Example 5

Preparation of Compound A Benzenesulfonate (1)

To a solution of Compound A free base (2.69 g) in 40 mL of EtOAc was added 1.31 g of benzenesulfonic acid monohydrate was added, and the mixture was stirred at room temperature for 1 hour. The resulting precipitates were collected by filtration. To a suspension of the precipitates in 30 mL of 2-butanone was added 0.35 mL of water. The resulting mixture was heated to be dissolved. After cooling to room temperature, the mixture was stirred for 60 hours. The resulting crystals were collected by filtration to give 2.49 g of the title compound as white crystals.

$^1$H-NMR(DMSO-$d_6$: 70° C.): 1.65–1.99 (4H, m), 2.23 (1H, brs), 2.77–2.96 (2H, m), 3.06–3.32 (5H, m), 3.44 (1H, ddd, J=13.6, 8.4, 5.2 Hz), 3.66 (1H, dd, J=13.6, 8.4 Hz), 3.91 (1H, dt, J=12.8, 5.6 Hz), 4.97 (1H, dt, J=8.4, 4.4 Hz), 6.25 (1H, s), 7.11–7.35 (12H, m), 7.59–7.64 (2H, m), 9.39 (1H, brs).

Peak top temperature of endothermia in DSC: 178° C.

Figure 21:
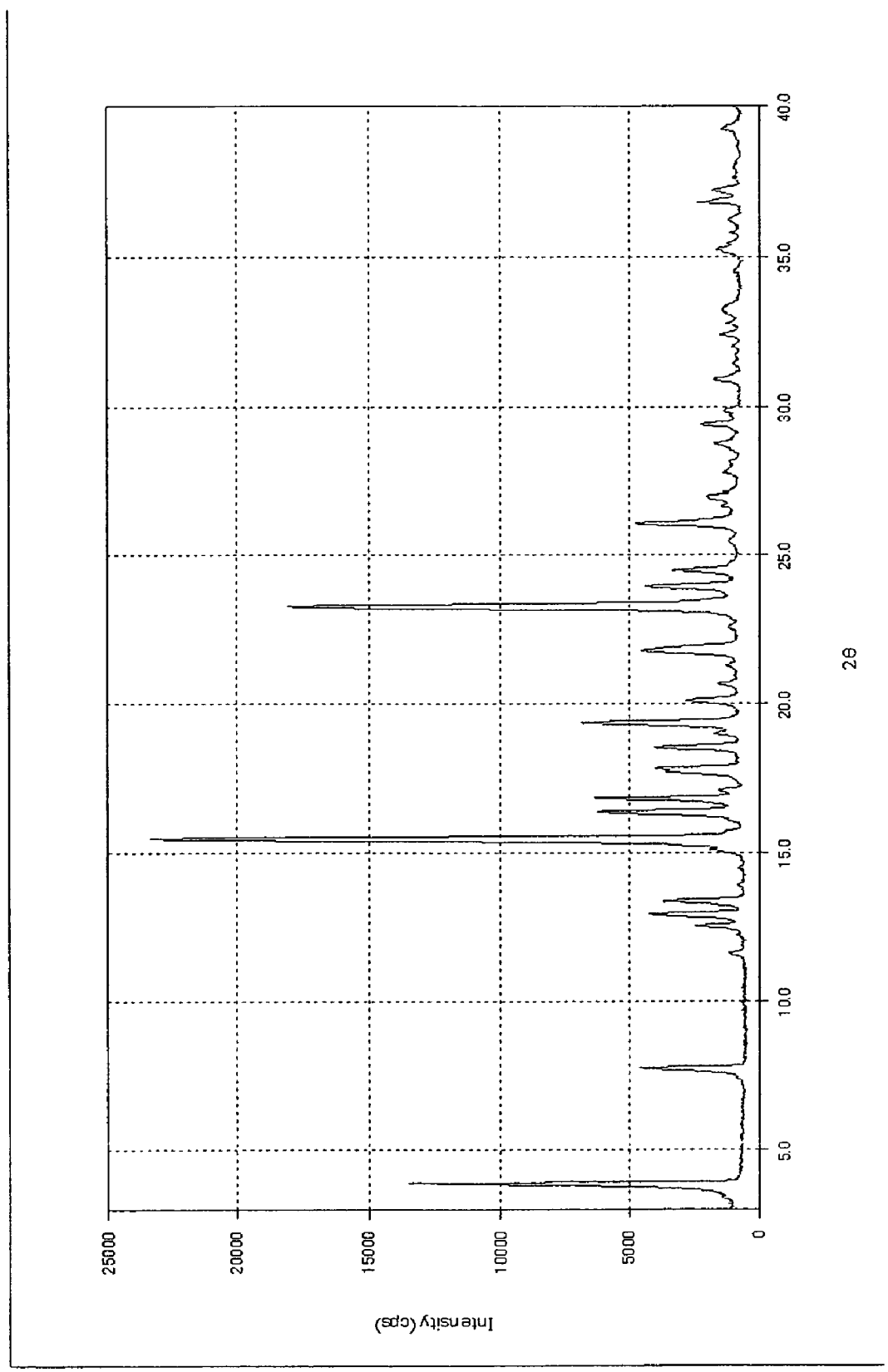
FIG. 21 shows a powder X-ray diffraction pattern of the compound of Example 5.

FIG. 21 shows a powder X-ray diffraction pattern of the compound in Example 5.

Example 5-1

Preparation of Compound A Benzenesulfonate (2)

To a solution of Compound A free base (7.00 g) in 70 mL of acetone were added 3.40 g of benzenesulfonic acid monohydrate and 70 mL of tert-butyl methyl ether, and the mixture was stirred using a mechanical stirrer at room temperature for 9 hours. The resulting precipitates were collected by filtration to give 8.10 g of the title compound as white crystals.

The $^1$H-NMR spectrum of the product was identical with that of Example 5, but the DSC and the powder X-ray diffraction pattern suggested that the products of Example 5 and Example 5-1 showed crystal polymorphism.

Peak top temperature of endothermia in DSC: 170° C.

Figure 22:
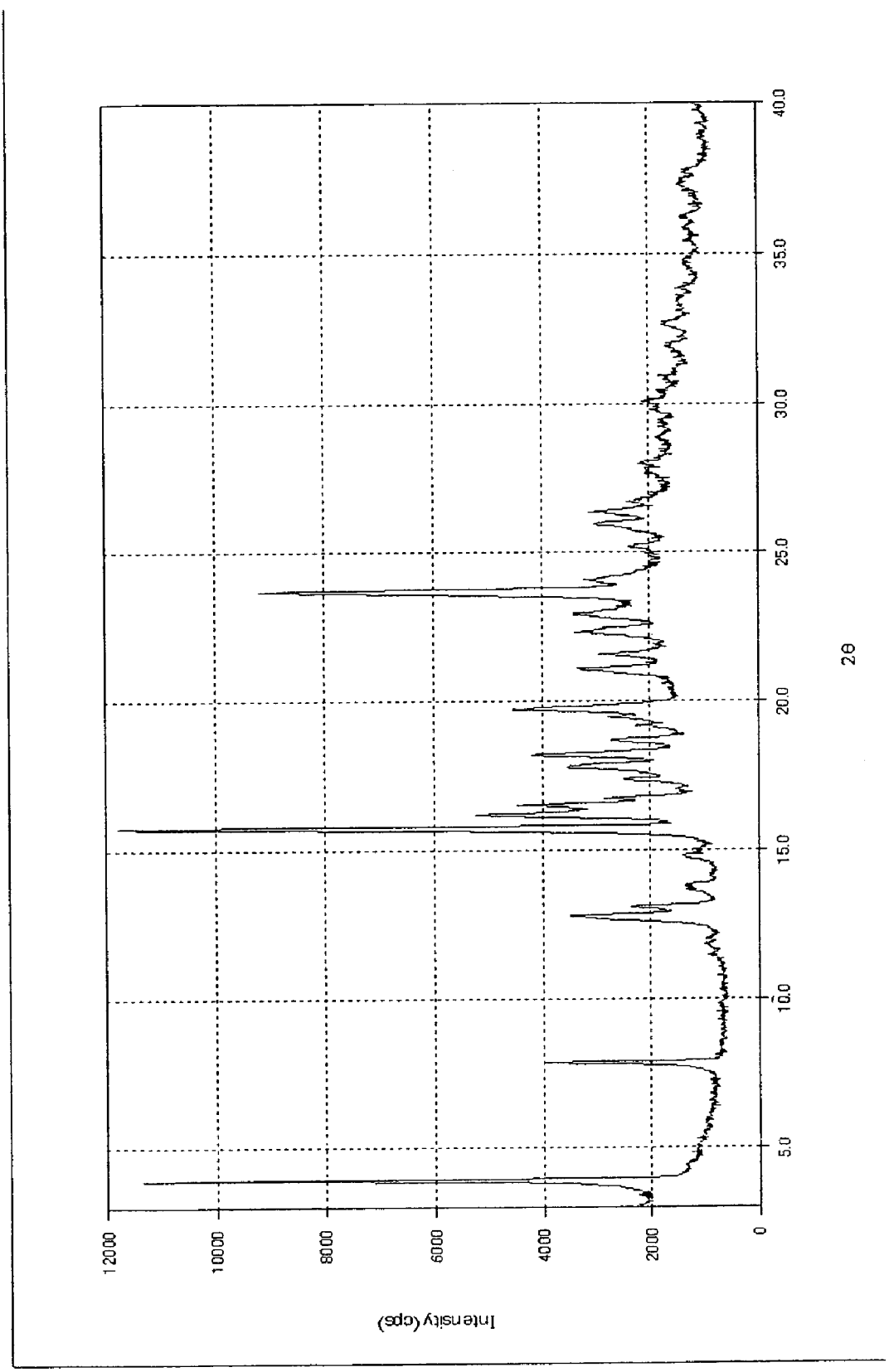
FIG. 22 shows a powder X-ray diffraction pattern of the compound of Example 5-1.

FIG. 22 shows a powder X-ray diffraction pattern of the compound in Example 5-1.

Example 6

Preparation of Compound A Cyclohexanesulfamate

To a solution of Compound A free base (500 mg) in 5 mL of 2-PrOH was added 494 mg of cyclohexanesulfamic acid, and the mixture was stirred at room temperature for 13 hours. The resulting precipitates were collected by filtration to give 550 mg of the title compound as white crystals.

$^1$H-NMR(DMSO-$d_6$: 70° C.): 1.00–1.35 (10H, m), 1.46–2.08 (14H, m), 2.23 (1H, brs), 2.77–3.30 (11H, m), 3.44 (1H, ddd, J=13.6, 8.8, 5.2 Hz), 3.64 (1H, dd, J=13.8, 8.8 Hz), 3.91 (1H, dt, J=12.8, 5.6 Hz), 4.96 (1H, dt, J=8.4, 4.4 Hz), 6.25 (1H, s), 7.10–7.36 (9H, m).

Peak top temperature of endothermia in DSC: 127° C. and 170° C.

Figure 23:
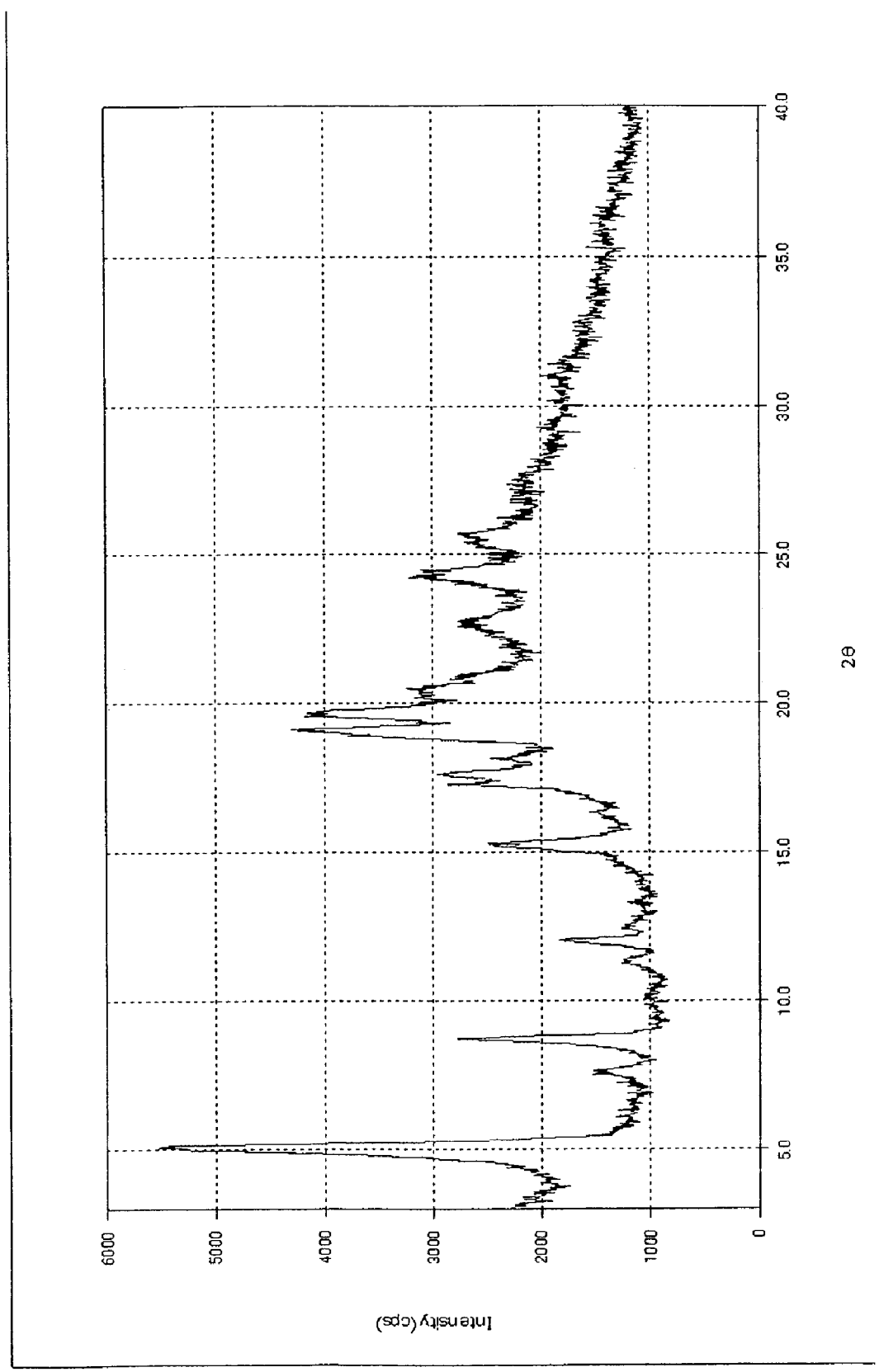
FIG. 23 shows a powder X-ray diffraction pattern of the compound of Example 6.

FIG. 23 shows a powder X-ray diffraction pattern of the compound in Example 6.

Example 7

Preparation of Compound A Hydrobromide

To a solution of Compound A free base (200 mg) in 1.0 mL of ETOH was added 95 mg of 47% hydrobromic acid. To the reaction mixture, 1.1 mL of diisopropyl ether was added with stirring, and the resulting mixture was stirred at 5° C. for 18 hours. The obtaining precipitates were collected by filtration to give 165 mg of the title compound as white crystals.

$^1$H-NMR(DMSO-$d_6$: 70° C.): 1.65–1.98 (4H, m), 2.24 (1H, brs), 2.77–2.97 (2H, m), 3.05–3.35 (5H, m), 3.45 (1H, ddd, J=13.6, 8.8, 5.2 Hz), 3.65 (1H, dd, J=13.2, 8.4 Hz), 3.91 (1H, dt, J=12.8, 5.6 Hz), 4.97 (1H, dt, J=8.8, 4.4 Hz), 6.26 (1H, s), 7.11–7.35 (9H, m), 9.68 (1H, brs).

Elemental Analysis: (calculated for $C_{23}H_{26}N_2O_2 \cdot HBr$) C, 62.31; H, 6.14; N, 6.32; Br, 18.02. (found) C, 62.04; H, 6.10; N, 6.09; Br, 17.73.

Peak top temperature of endothermia in DSC: 199° C.

Figure 24:
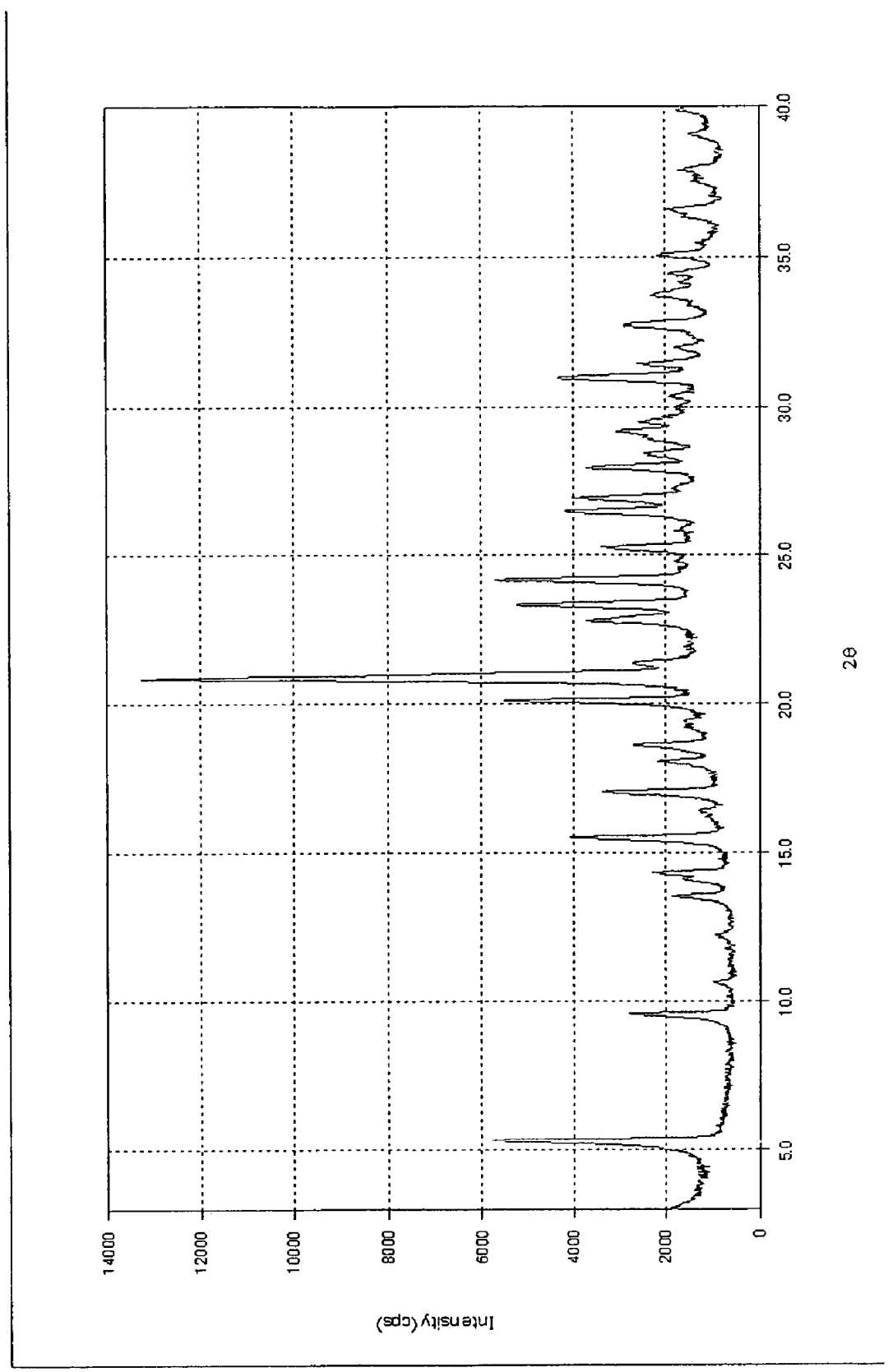
FIG. 24 shows a powder X-ray diffraction pattern of the compound of Example 7.

FIG. 24 shows a powder X-ray diffraction pattern of the compound in Example 7.

Example 8

Preparation of Compound A naphthalene-2-sulfonate

To a solution of Compound A free base (100 mg) in 1.0 mL of EtOH was added 65 mg of naphthalene-2-sulfonic acid hydrate, and the mixture was stirred for 26 hours. The resulting crystals were collected by filtration to give 79 mg of the title compound as slightly grey crystals.

$^1$H-NMR(DMSO-$d_6$: 70° C.): 1.65–2.00 (4H, m), 2.24 (1H, brs), 2.77–2.97 (2H, m), 3.05–3.32 (5H, m), 3.45 (1H, ddd, J=14.0, 9.2, 5.2 Hz), 3.65 (1H, dd, J=14.0, 8.8 Hz), 3.90 (1H, dt, J=12.8, 5.6 Hz), 4.97 (1H, dt, J=8.0, 4.4 Hz), 6.25 (1H, s), 7.12–7.34 (9H, m), 7.49 (2H, dt, J=10.4, 4.0 Hz), 7.74 (1H, dd, J=8.4, 1.6 Hz), 7.82 (1H, d, J=8.0 Hz), 7.85–7.95 (2H, m), 8.14 (1H, s), 9.35 (1H, brs).

Peak top temperature of endothermia in DSC: 178° C.

Figure 25:
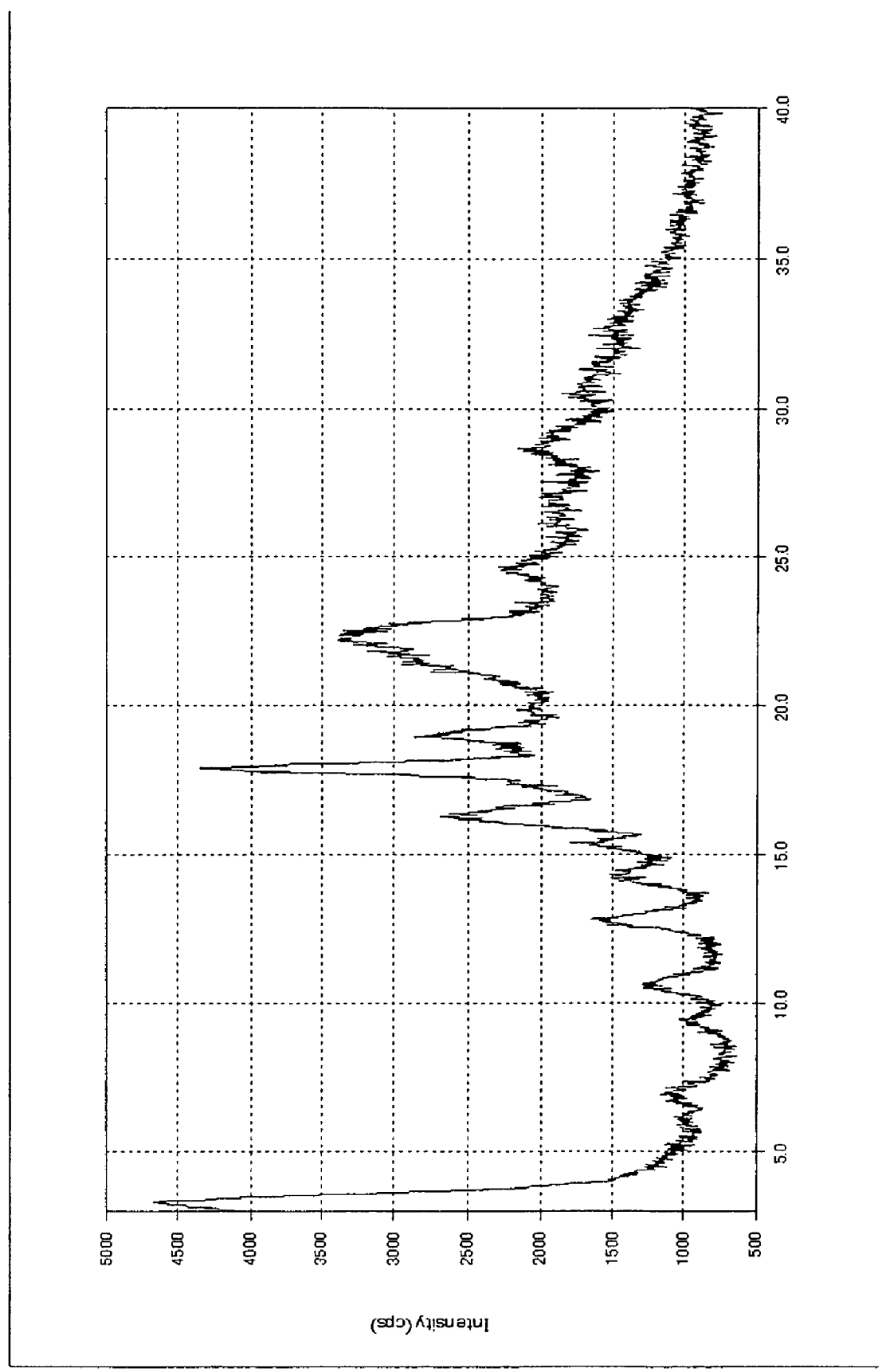
FIG. 25 shows a powder X-ray diffraction pattern of the compound of Example 8.

FIG. 25 shows a powder X-ray diffraction pattern of the compound in Example 8.

Example 9

Preparation of Compound A Sebacate

To a solution of Compound A free base (300 mg) in 1.0 mL of EtOH was added 171 mg of sebacic acid, and the mixture was stirred for 3 hours. The resulting crystals were collected by filtration and washed with ethanol to give 165 mg of the title compound as white crystals.

$^1$H-NMR(DMSO-$d_6$: 26.1° C.): 1.16–2.00 (17H, m), 2.17 (4H, t, J=7.2), 2.50–2.97 (7H, m), 3.02–3.08 (1H, m), 3.28–3.50 (1H, m), 3.78–3.98 (1H, m), 4.65 (1H, brs), 6.24 (1H, brs), 7.12–7.26 (10H, m).

Peak top temperature of endothermia in DSC: 127° C.

Figure 26:
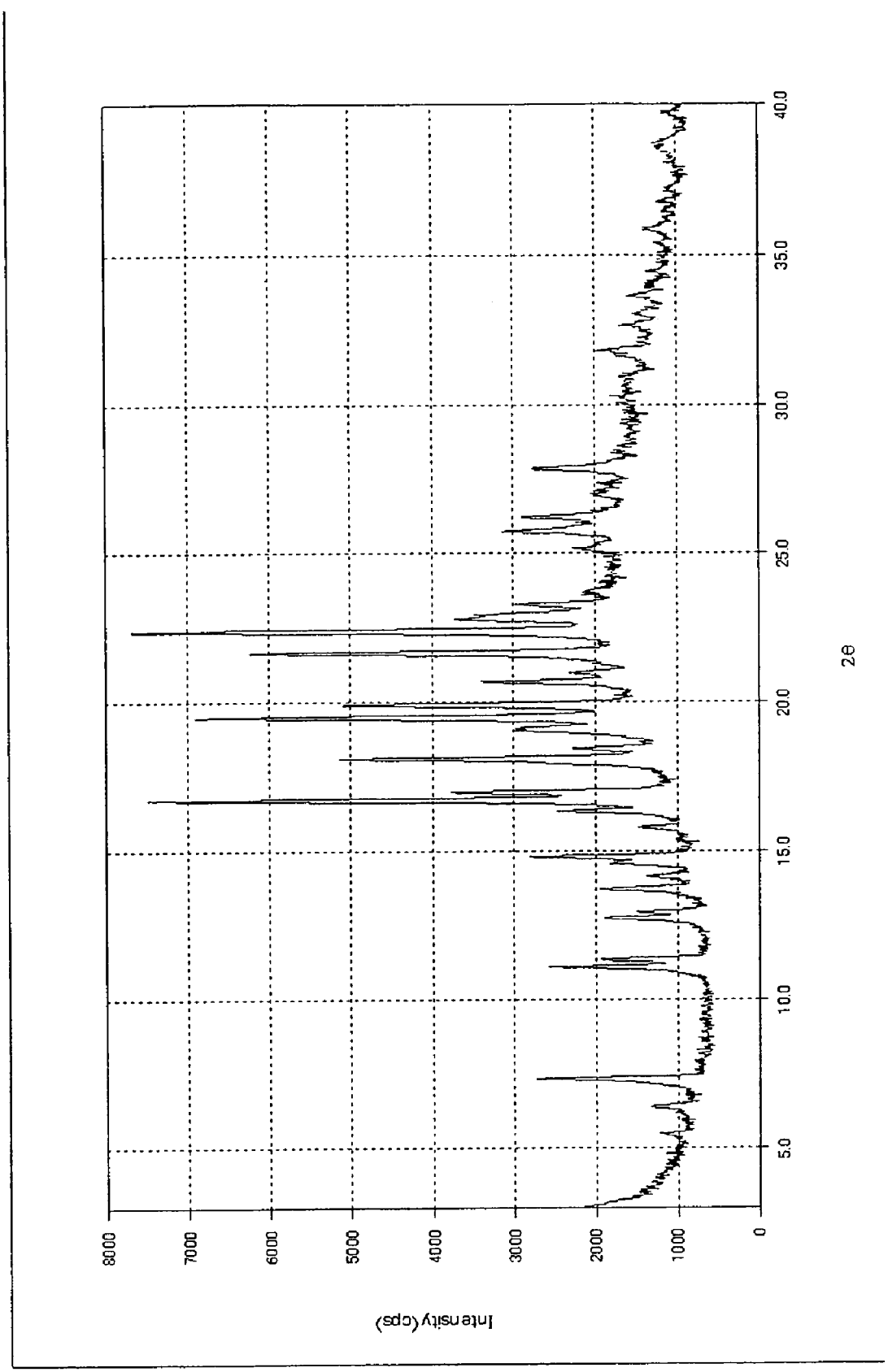
FIG. 26 shows a powder X-ray diffraction pattern of the compound of Example 9.

FIG. 26 shows a powder X-ray diffraction pattern of the compound in Example 9.

Example 10

Preparation of Compound A
(+)-camphor-10-sulfonate

To a solution of Compound A free base (200 mg) in 2 mL of acetone was added 138 mg of (+)-camphor-10-sulfonic acid, and the mixture was stirred at room temperature for 5 hours. The resulting precipitates were collected by filtration to give 191 mg of the title compound as white crystals.

$^1$H-NMR(DMSO-$d_6$: 70° C.): 0.76 (3H, s), 1.08 (3H, s), 1.20–1.33 (2H, m), 1.65–1.98 (7H, m), 2.18–2.28 (2H, m), 2.37–2.42 (1H, m), 2.65–2.97 (4H, m), 3.05–3.31 (5H, m), 3.44 (1H, ddd, J=13.6, 8.8, 4.8 Hz), 3.65 (1H, dd, J=13.6, 8.4 Hz), 3.91 (1H, dt, J=13.2, 5.6 Hz), 4.97 (1H, dt, J=8.8, 4.4 Hz), 6.25 (1H, s), 7.11–7.35 (9H, m), 9.44 (1H, brs).

Peak top temperature of endothermia in DSC: 198° C.

Figure 27:
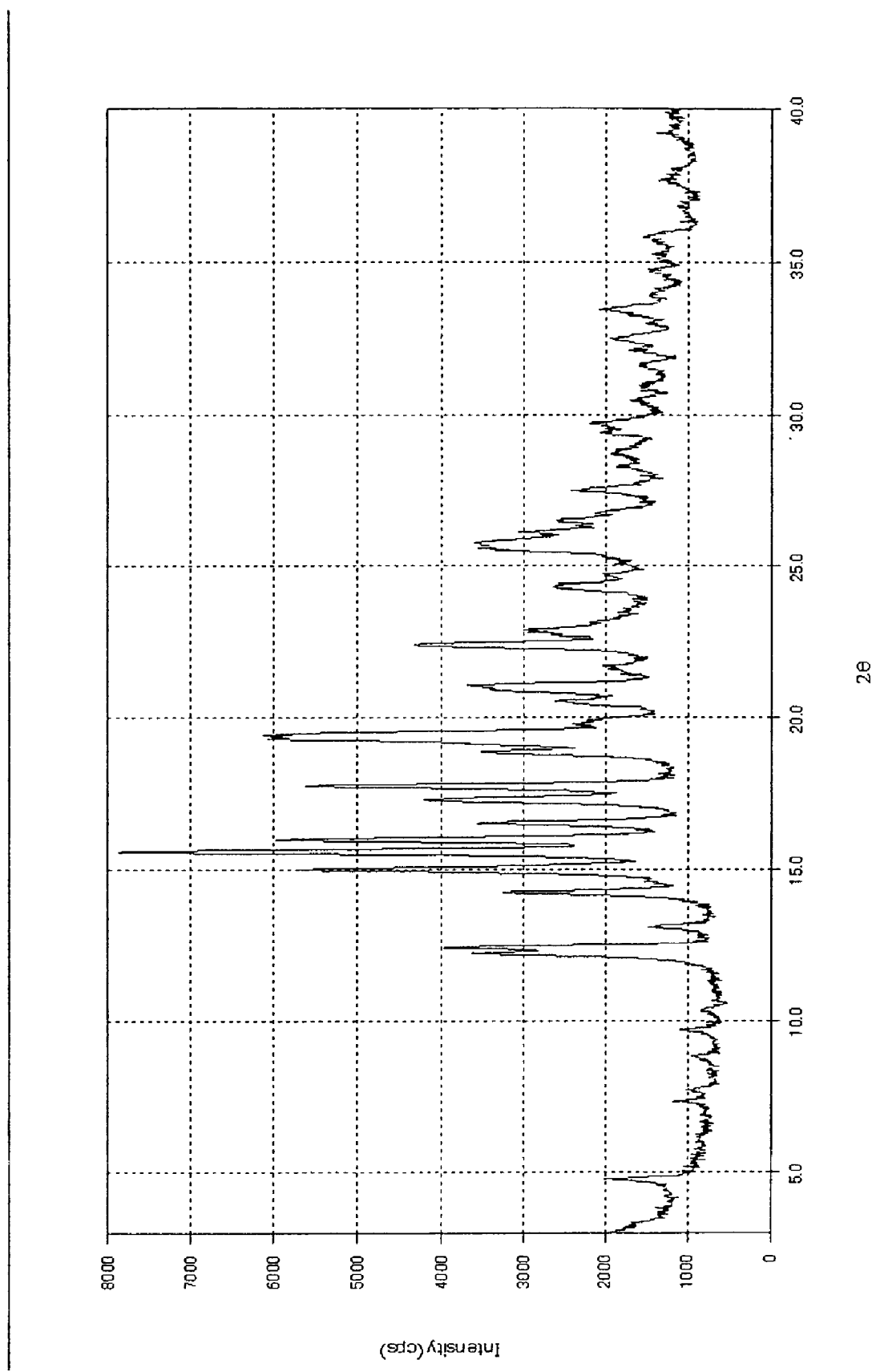
FIG. 27 shows a powder X-ray diffraction pattern of the compound of Example 10.

FIG. 27 shows a powder X-ray diffraction pattern of the compound in Example 10.

Example 11

Preparation of Compound A p-Toluenesulfonate

To a solution of Compound A free base (200 mg) in a mixture of 1.5 mL of acetone and 0.5 mL of tert-butyl methyl ether was added 105 mg of p-toluenesulfonic acid monohydrate, and the mixture was stirred at room temperature for 17 hours. The resulting precipitates were collected by filtration to give 83 mg of the title compound as white crystals.

$^1$H-NMR(DMSO-$d_6$:70° C.): 1.65–2.00 (4H, m), 2.24 (1H, brs), 2.28 (3H, s), 2.76–2.96 (2H, m), 3.05–3.30 (5H, m), 3.44 (1H, ddd, J=13.6, 8.0, 5.0 Hz), 3.65 (1H, dd, J=13.6, 8.0 Hz), 3.91 (1H, dt, J=12.8, 5.6 Hz), 4.97 (1H, dt, J=8.4, 4.4 Hz), 6.25 (1H, s), 7.09 (2H, d, J=7.6 Hz), 7.11–7.35 (9H, m), 7.47–7.52 (2H, m), 9.38 (1H, brs).

Peak top temperature of endothermia in DSC: 150° C.

Figure 28:
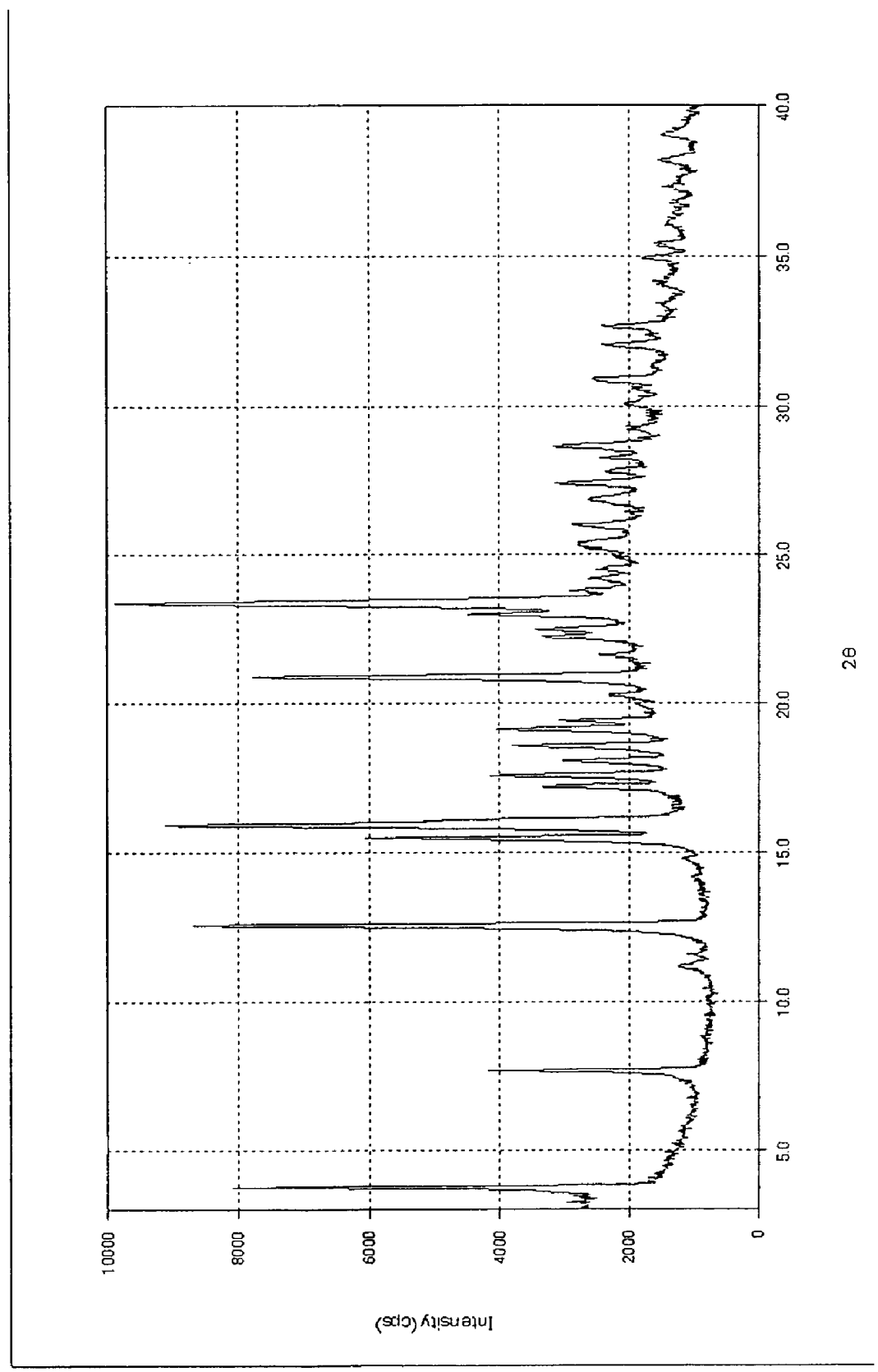
FIG. 28 shows a powder X-ray diffraction pattern of the compound of Example 11.

FIG. 28 shows a powder X-ray diffraction pattern of the compound in Example 11.

Example 12

Preparation of Compound A Ethanesulfonate

To a solution of Compound A free base (100 mg) in 1.0 mL of 2-butanone was added 31 mg of ethanesulfonic acid, and the mixture was stirred at room temperature for 6.5 hours. The resulting precipitates were collected by filtration to give 95 mg of the title compound as white crystals.

$^1$H-NMR(DMSO-$d_6$:70° C.): 1.07 (3H, t, J=7.6 Hz), 1.62–2.10 (4H, m), 2.24 (1H, brs), 2.39 (2H, q, J=7.6 Hz), 2.76–2.96 (2H, m), 3.08–3.32 (5H, m), 3.44 (1H, ddd, J=13.6, 8.8, 4.8 Hz), 3.65 (1H, dd, J=13.6, 8.8 Hz), 3.91 (1H, dt, J=12.4, 5.2 Hz), 4.92–5.02 (1H, m), 6.25 (1H, s), 7.10–7.35 (9H, m), 9.51 (1H, brs).

Peak top temperature of endothermia in DSC: 233° C.

Figure 29:
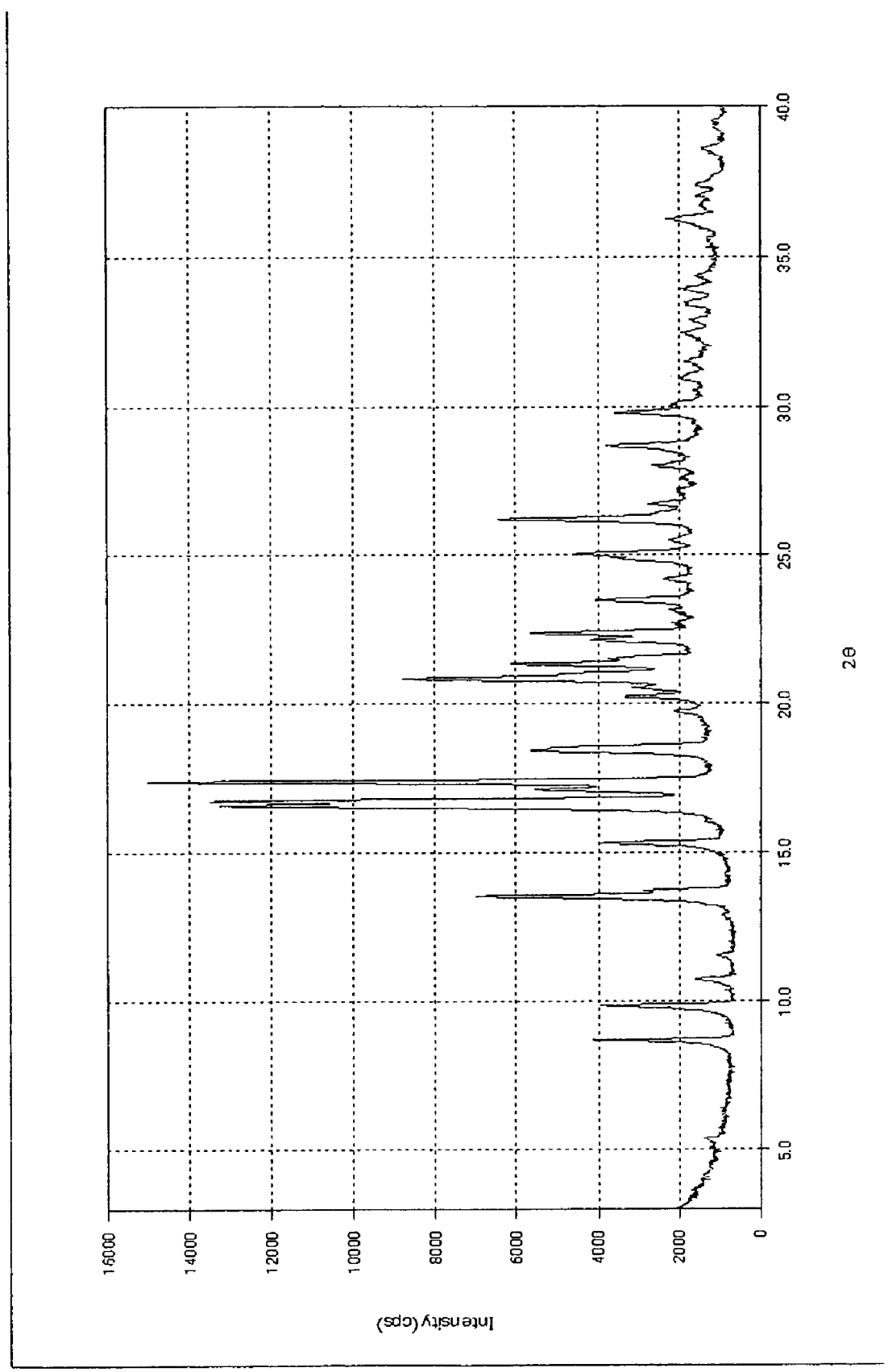
FIG. 29 shows a powder X-ray diffraction pattern of the compound of Example 12.

FIG. 29 shows a powder X-ray diffraction pattern of the compound in Example 12.

Example 13

Preparation of Compound A Methanesulfonate

To a solution of Compound A free base (200 mg) in 1.0 mL of 2-butanone was added a solution of 53 mg of methanesulfonic acid in 1.0 mL of iPrOAc, and the mixture was stirred at room temperature for 0.5 hours. The resulting precipitates were collected by filtration to give 187 mg of the title compound as white crystals.

$^1$H-NHR(DMSO-$d_6$:70° C.): 1.62–2.02 (4H, m), 2.24 (1H, brs), 2.30 (3H, s), 2.76–2.96 (2H, m), 3.00–3.34 (5H, m), 3.44 (1H, ddd, J=13.6, 8.8, 4.8 Hz), 3.65 (1H, dd, J=13.6, 8.6 Hz), 3.91 (1H, dt, J=13.2, 5.2 H,z), 4.90–5.40 (1H, m), 6.25 (1H, s), 7.08–7.36 (9H, m), 9.37 (1H, brs).

Peak top temperature of endothermia in DSC: 178° C.

Figure 30:
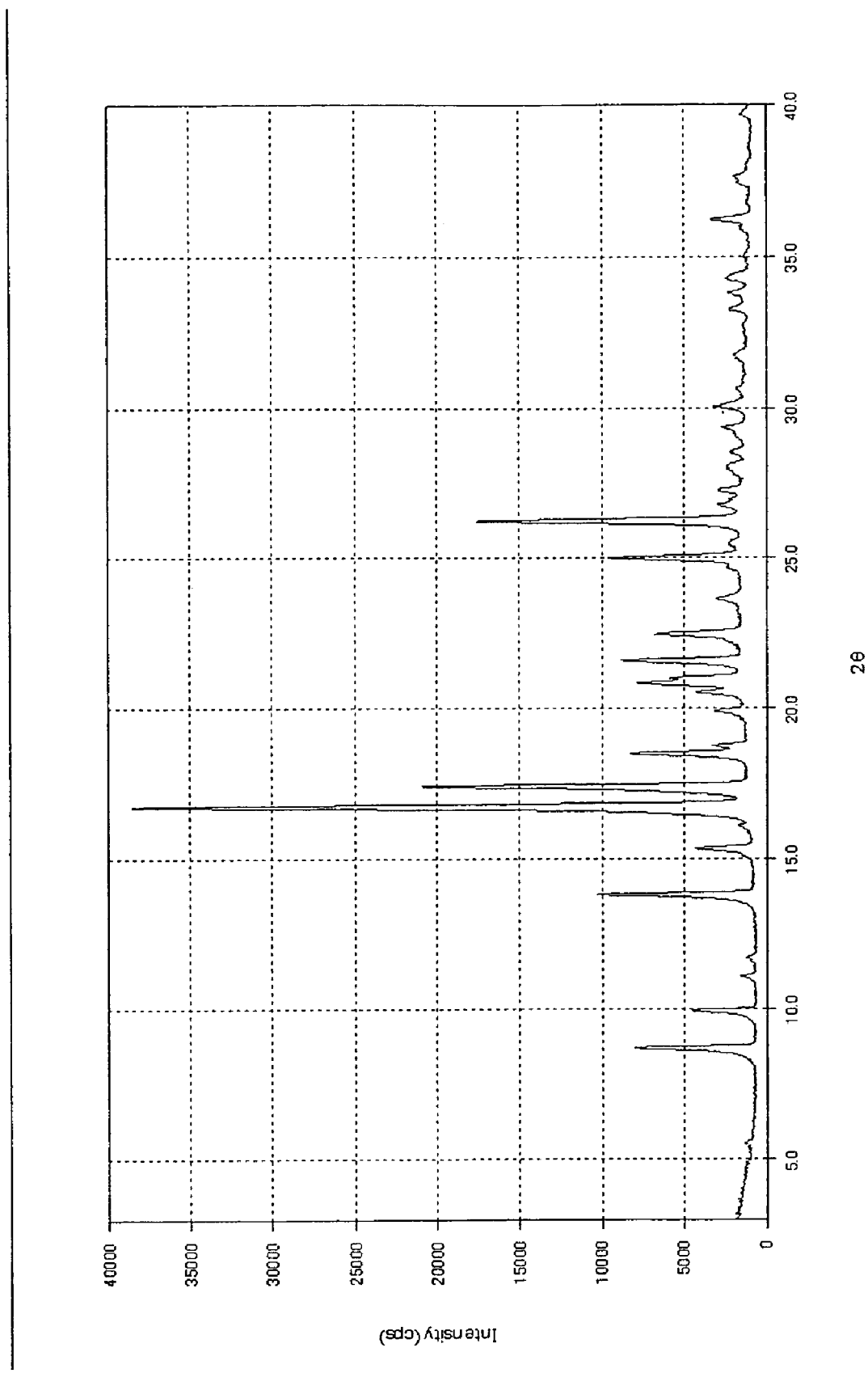
FIG. 30 shows a powder X-ray diffraction pattern of the compound of Example 13.

FIG. 30 shows a powder X-ray diffraction pattern of the compound in Example 13.

Example 14

Preparation of Compound A Methyl Phosphate

To a solution of Compound A free base (200 mg) in 2.0 mL of EtOAc and 0.5 mL of 2-butanone was added 98 mg of methyl phosphate, and the mixture was stirred at room temperature for 22 hours. The resulting precipitates were collected by filtration to give 124 mg of the title compound as white crystals.

$^1$H—NHR(DMSO-$d_6$:70° C.): 1.43–1.54 (1H, m), 1.57–1.81 (3H, m), 2.01–2.10 (1H, m), 2.77–2.99 (7H, m), 3.29–3.46 (2H, m), 3.42 (3H, d, J=10.8 Hz), 3.90 (1H, dt, J=13.2, 5.6 Hz), 4.76–4.84 (1H, m), 6.24 (1H, s), 7.12–7.33 (9H, m).

Peak top temperature of endothermia in DSC: 195° C.

Figure 31:
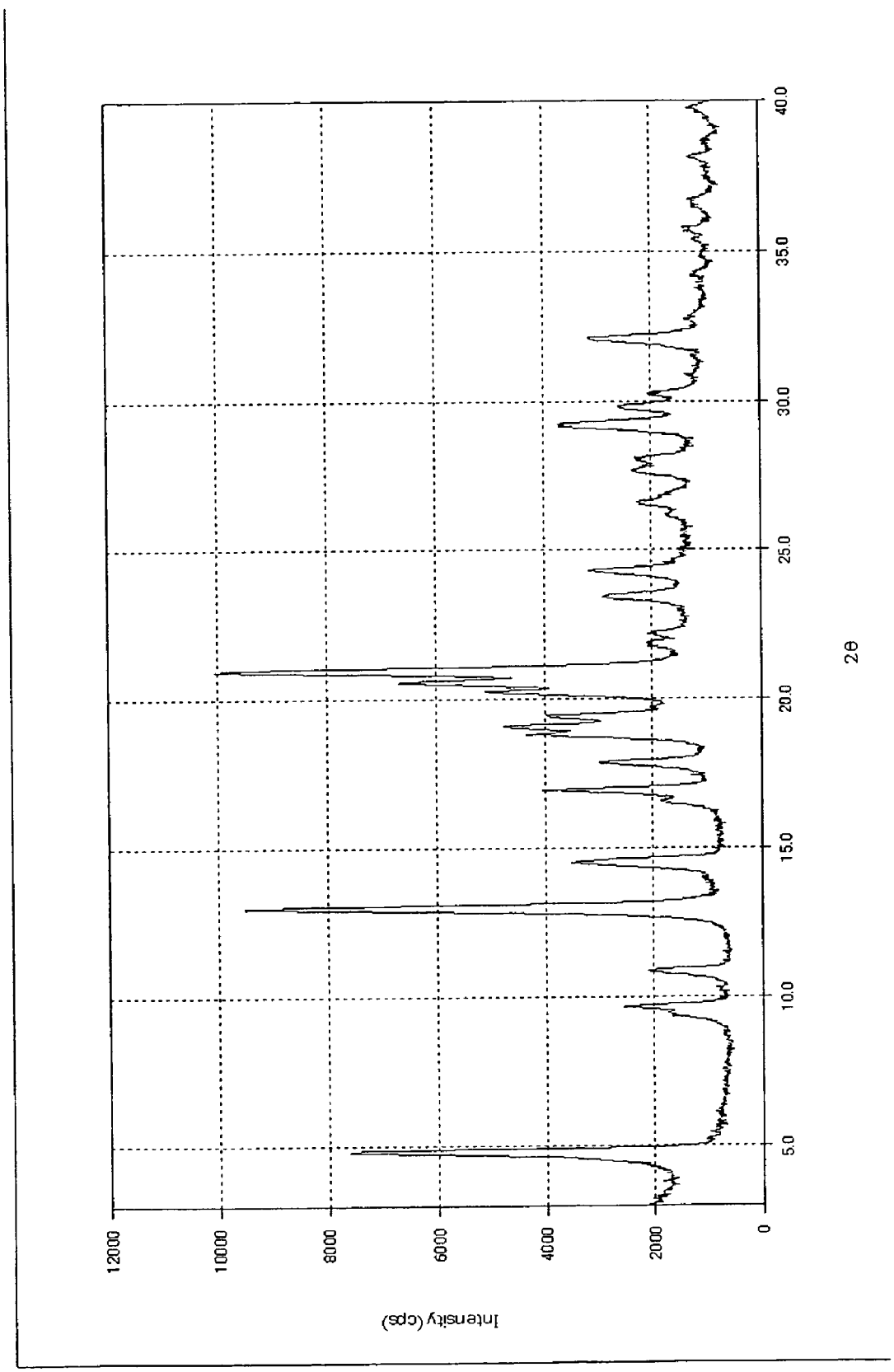
FIG. 31 shows a powder X-ray diffraction pattern of the compound of Example 14.

FIG. 31 shows a powder X-ray diffraction pattern of the compound in Example 14.

The effect of the acid addition salt of Compound A of the invention was confirmed by the following Test Examples.

Test Example 1

Evaluation of Hygroscopicity

A sample (about 5 mg) was placed in a purpose-made quartz holder, and the sample weight at the respective humidity was continuously measured and recorded in the following conditions. The apparatus including data processing was operated according to the method and procedure directed in each device. (Apparatus: dynamic steam adsorption measuring apparatus DVS Advantage, made by SMS)

(Condition)

Measuring temperature: 25° C.; drying before measurement: not done; humidity at the beginning: 5% RH; maximum humidity: 95% RH; humidity at the end: 5% RH; step: 5% RH; equilibrium standard: 0.03 wt % in 5 min; maximum equilibrated time: 180 min; sampling interval: 20 sec; data recording interval: 1 min The charts obtained in these tests are shown in FIG. 1 to FIG. 14. The weight change within the range of measuring condition is shown in Table 1.

TABLE 1

| Compound tested | Weight Change (%) |
|---|---|
| Example 1 | <1 |
| Example 2 | <1 |
| Example 3 | <1 |
| Example 4 | <2 |
| Example 5 | <1 |
| Example 5-1 | <1 |
| Example 6 | <3 |
| Example 7 | <4 |
| Example 8 | <4 |
| Example 9 | <1 |
| Example 10 | <2 |
| Example 11 | <6 |
| Example 12 | <5 |
| Example 13 | <25 |
| Example 14 | <11 |
| Reference Example 2 | >35 (deliquescent) |

As shown in FIG. 1 and Table 1, Compound A hydrochloride which is a known compound began to rapidly take up moisture at about 65% relative humidity and the absorption of moisture was recognized as a weight gain of 15% or more at 75% or more relative humidity. The weight change exceeded 35% within the range of measuring condition, i.e., 5–95% relative humidity, and this change was accompanied by deliquescence. On the other hand, as shown in FIG. 2 to FIG. 16 and Table 1, the acid addition salts of Compound A of the invention was confirmed to have improved hydgroscopicity in comparison with the known Compound A hydrochloride and have much better properties as drugs or their drug substances.

Test Example 2

Evaluation of Stability (1)

A sample (about 0.5 mg) was weighed in a glass vial and applied to a forced degradation test in the following storage conditions.
Condition 1: 120° C.—tightly closed—24 hours
Condition 2: 25° C.—relative humidity 93%—open—5 days
Condition 3: 25° C.—NUV (near ultraviolet ray) irradiated—tightly closed—5 days A sample after storage was dissolved in 1 mL of MeOH and used as a sample solution. The sample solution was diluted 100 times with MeOH and used as a standard solution. Impurities contained in the sample solution was quantitatively analyzed using the standard solution. In this determination, the apparatus including data processing was operated according to the method and procedure directed in each device. (Apparatus: LC-MSD 1100 series, made by Agilent)

The test results are shown in Table 2.

TABLE 2

| | Impurities before Storage (%) | Change from Impurity Amt. before Storage (%) | | |
|---|---|---|---|---|
| | | Condition 1 | Condition 2 | Condition 3 |
| Example 1 | 1.5 | 0.2 | −0.1 | −0.3 |
| Example 2 | 0.0 | 0.2 | 0.1 | 0.0 |
| Example 3 | 0.0 | 2.3 | 0.1 | 0.0 |
| Example 4 | 1.9 | 50.8 | −0.3 | −0.3 |
| Example 5 | 1.6 | 0.3 | 0.1 | −0.1 |
| Example 5-1 | 1.8 | −0.1 | 0.0 | −0.2 |
| Example 6 | 1.4 | 8.1 | 0.0 | 0.1 |
| Example 7 | 0.5 | −0.2 | 0.2 | 0.3 |
| Example 8 | 2.0 | 1.3 | 0.2 | 2.6 |
| Example 9 | 3.7 | −0.3 | 0.2 | −0.8 |
| Example 10 | 0.9 | 0.0 | 0.0 | 0.0 |
| Example 11 | 0.5 | −0.1 | 0.1 | 0.0 |
| Example 12 | 1.4 | −0.2 | −0.1 | −0.1 |
| Reference Example 2 | 0.1 | 0.2 | 3.8 | 2.0 |

Test Example 3

Evaluation of Stability (2)

A sample (about 5 mg) was weighed in a glass mess-flask of 10 mL and applied to a stress testing in the following storage conditions.
Condition 1: 5° C.—shading—tightly closed
Condition 2: 40° C.—relative humidity 75%—open
Condition 3: 60° C.—shading—tightly closed
Condition 4: 80° C.—shading—tightly closed
Condition 5: 25° C.—D65 (1000 lux)—tightly closed Chemical stability: After storage, MeOH was placed in the mess-flask containing the sample up to the level of the marked line, and the resulting solution was used as a sample solution. The sample solution was diluted 100 times with MeOH to prepare a standard solution, which was used in determination of impurities contained in the sample solution. Detection of the impurities was performed by means of UV at 210 nm. The apparatus including data processing was operated according to the method and procedure directed in each device. (Apparatus: LC-MSD 1100 series, made by Agilent)

The test results are shown in Table 3.

TABLE 3

| | | Impurities (%) | |
|---|---|---|---|
| Test Condition | Term | Example 1 | Reference Example 2 |
| Condition 1 | 2 weeks | 0.00 | 0.25 |
| | 1 month | 0.00 | 0.21 |
| | 2 months | 0.00 | 0.18 |
| Condition 2 | 2 weeks | 0.00 | 8.72 |
| | 1 month | 0.00 | 8.19 |
| | 2 months | 0.00 | 9.20 |
| Condition 3 | 2 weeks | 0.00 | 0.34 |
| | 1 month | 0.00 | 0.22 |
| | 2 months | 0.00 | 0.24 |
| Condition 4 | 2 weeks | 0.00 | 0.43 |
| | 1 month | 0.00 | 0.39 |
| | 2 months | 0.00 | 0.47 |
| Condition 5 | 2 weeks | 0.00 | 1.73 |
| | 1 month | 0.00 | 2.38 |
| | 2 months | 0.00 | 3.68 |

As shown in Table 2 and Table 3, it was found that impurities increased during storage in Compound A hydrochloride which was a known compound. In particular, it became clear that Compound A hydrochloride is not so stable to humidity (Condition 2 in Test Example 2 and Condition 2 in Test Example 3) and light (Condition 3 in Test Example 2 and Condition 5 in Test Example 3). On the other hand, as shown in Table 2 and Table 3, it was confirmed that the acid addition salts of the invention showed almost no increase of impurities, indicating it being chemically and physically highly stable in comparison with the known Compound A hydrochloride and have much better properties as drugs or their drug substances. In this connection, the reason of the increase of impurities recognized in the compounds of Example 4 and Example 6 was considered that they have somewhat low melting points that they melted under Condition 1 of Test Example 2 (stability test to heat) or the preserved condition was near the melting point.

Test Example 4

Functional Affinity Estimate for Muscarinic $M_3$ Receptors in Bladders

According to a method as described by Ikeda et al., (2002, Naunyn-Schmiedeberg's Archives of Pharmacology, Vol. 366, p. 97–103), functional affinity estimates of test compound for muscarinic $M_3$ receptors were determined using changes in intracellular $Ca^{2+}$. Below, the method is described in brief.

Smooth muscle cells were isolated from guinea pig bladders from which the epidermis had been removed, loaded with a calcium-sensitive fluorescent dye Fura2 and suspended in phenol red-free Hanks' buffer solution supplemented with 20 mM HEPES (pH 7.4) and 0.1% bovine serum albumin. An aliquot of cell suspension (490 μL) was continuously stirred, kept at 28° C. and monitored for the ratio of fluorescence (500 nm) at 340 nm excitation to that at 380 nm excitation. To each aliquot, 5 μL of test compound and carbachol solutions were serially added with a 2 minute interval, and the peak increase in the ratio over the level just before stimulation was used in data analysis. The concentration required for 50% stimulation or 50% inhibition, that is, $EC_{50}$ or $IC_{50}$, was obtained by sigmoidal curve fitting, then $IC_{50}$ values of test compound were converted into Ki values based on the $EC_{50}$ value of carbachol using the Cheng-Prusoff equation.

Table 4 shows the results.

TABLE 4

| Compound Tested | $IC_{50}$ (ng/mL) | Ki (nM) |
|---|---|---|
| Example 1 | 2.4 ± 0.75 | 0.68 ± 0.21 |
| Example 2 | 3.2 ± 0.97 | 0.62 ± 0.16 |
| Example 3 | 3.8 ± 1.2 | 0.69 ± 0.19 |
| Example 4 | 2.5 ± 0.044 | 0.66 ± 0.046 |
| Example 5 | 1.8 ± 0.79 | 0.47 ± 0.12 |
| Example 6 | 4.3 ± 1.2 | 0.84 ± 0.10 |
| Example 7 | 1.8 ± 0.49 | 0.66 ± 0.28 |
| Example 8 | 2.3 ± 0.87 | 0.55 ± 0.12 |
| Example 9 | 2.2 ± 0.33 | 0.56 ± 0.048 |
| Example 10 | 2.6 ± 0.42 | 0.65 ± 0.12 |
| Example 11 | 2.2 ± 0.87 | 0.52 ± 0.13 |
| Example 12 | 1.9 ± 0.30 | 0.54 ± 0.055 |

As shown above, the acid addition salts of Compound A of the present invention proved to have the affinity for muscarinic $M_3$ receptors that is sufficient for their use as a medicine.

Test Example 5

Inhibitory Effects on Carbachol-Evoked Bladder Contraction in Anesthetized Mice

The method for determination of inhibitory effects of test compounds on bladder contraction is described as follows.

Female mice, weighing 30 to 35 g, were anesthetized with a sub-lethal dose (75 mg/kg, i.v.) of sodium pentobarbital and placed supine on a heating pad to maintain the body temperature. A polyethylene catheter (PE10) was cannulated to the bladder via the urethra and secured by purse-string suture at the external urethral opening. Another catheter was inserted into the femoral vein for injections of drug solutions at a 3 mL volume. The bladder catheter was connected to a pressure transducer through a three-way stopcock valve. The bladder was emptied by drainage of urine through the catheter, and then distended with about 100 μL of physiological saline, and the intravesical pressure was measured.

After intravesical pressure stabilization, the muscarinic agonist carbachol (10 μg/kg) was administered repeatedly with an interval of 15 minutes or longer. By this means, bladder contractions occurred in a reproducible manner over 2 hours without deterioration of physical conditions. After three responses to carbachol were obtained, a test compound injection was followed by carbachol administration 10 minutes later and this procedure was repeated with increasing doses of the test compound. In four or five mice per test compound, the percent inhibition of means of prior drug responses was obtained and the dose of test compound required for 50% inhibition ($ID_{50}$) was estimated by the linear regression analysis. Mice showing rhythmic bladder constriction were not used for the data analysis.

Following $ID_{50}$ values were obtained: 0.079 mg/kg for Example 1, 0.090 mg/kg for Example 4, 0.059 mg/kg for Example 5, 0.050 mg/kg for Example 7, and 0.057 mg/kg for Example 8.

The result clearly suggest that the acid addition salts of Compound A of the present invention have inhibitory effects on contraction of the bladder induced by the muscarinic agonist carbachol.

The invention claimed is:

1. An acid addition salt consisting of (−)-(3R)-quinuclidin-3-yl (1R)-1-phenyl-1,2,3,4-tetrahydroisoquinoline-2-carboxylate with an acid selected from the group consisting of (−)-(2S,3S)-tartaric acid, (+)-(2S,3S)-di-O-benzoyltartaric acid, (+)-(2S,3S)-di-O-(4-methylbenzoyl)tartaric acid, (−)-L-phenylalanine, benzenesulfonic acid, cyclohexanesulfamic acid, hydrobromic acid, naphthalene-2-sulfonic acid, sebacic acid, (+)-camphor-10-sulfonic acid, p-toluenesulfonic acid, ethanesulfonic acid, methanesulfonic acid and methyl phosphate.

2. The acid addition salt according to claim 1, wherein the salt is (−)-(3R)-quinuclidin-3-yl(1R)-1-phenyl-1,2,3,4-tetrahydroisoquinoline-2-carboxylate (−)-(2S,3S)-tartrate.

3. The acid addition salt according to claim 1, wherein the salt is (−)-(3R)-quinuclidin-3-yl(1R)-1-phenyl-1,2,3,4-tetrahydroisoquinoline-2-carboxylate (+)-(2S,3S)-di-O-benzoyltartrate.

4. The acid addition salt according to claim 1, wherein the salt is (−)-(3R)-quinuclidin-3-yl(1R)-1-phenyl-1,2,3,4-tetrahydroisoquinoline-2-carboxylate (+)-(2S,3S)-di-O-(4-methylbenzoyl)tartrate.

5. The acid addition salt according to claim 1, wherein the salt is (−)-(3R)-quinuclidin-3-yl(1R)-1-phenyl-1,2,3,4-tetrahydroisoquinoline-2-carboxylate (−)-L-phenylalaninate.

6. The acid addition salt according to claim 1, wherein the salt is (−)-(3R)-quinuclidin-3-yl(1R)-1-phenyl-1,2,3,4-tetrahydroisoquinoline-2-carboxylate benzenesulfonate.

7. The acid addition salt according to claim 1, wherein the salt is (−)-(3R)-quinuclidin-3-yl(1R)-1-phenyl-1,2,3,4-tetrahydroisoquinoline-2-carboxylate cyclohexanesulfamate.

8. The acid addition salt according to claim 1, wherein the salt is (−)-(3R)-quinuclidin-3-yl(1R)-1-phenyl-1,2,3,4-tetrahydroisoquinoline-2-carboxylate hydrobromide.

9. The acid addition salt according to claim 1, wherein the salt is (−)-(3R)-quinuclidin-3-yl(1R)-1-phenyl-1,2,3,4-tetrahydroisoquinoline-2-carboxylate naphthalene-2-sulfonate.

10. The acid addition salt according to claim 1, wherein the salt is (−)-(3R)-quinuclidin-3-yl(1R)-1-phenyl-1,2,3,4-tetrahydroisoquinoline-2-carboxylate sebacate.

11. The acid addition salt according to claim 1, wherein the salt is (−)-(3R)-quinuclidin-3-yl(1R)-1-phenyl-1,2,3,4-tetrahydroisoquinoline-2-carboxylate (+)-camphor-10-sulfonate.

12. The acid addition salt according to claim 1, wherein the salt is (−)-(3R)-quinuclidin-3-yl(1R)-1-phenyl-1,2,3,4-tetrahydroisoquinoline-2-carboxylate p-toluenesulfonate.

13. The acid addition salt according to claim 1, wherein the salt is (−)-(3R)-quinuclidin-3-yl(1R)-1-phenyl-1,2,3,4-tetrahydroisoquinoline-2-carboxylate ethanesulfonate.

14. The acid addition salt according to claim 1, wherein the salt is (−)-(3R)-quinuclidin-3-yl(1R)-1-phenyl-1,2,3,4-tetrahydroisoquinoline-2-carboxylate methanesulfonate.

15. The acid addition salt according to claim 1, wherein the salt is (−)-(3R)-quinuclidin-3-yl(1R)-1-phenyl-1,2,3,4-tetrahydroisoquinoline-2-carboxylate methyl phosphate.

16. A pharmaceutical composition comprising one or more compounds mentioned in claim 1 as an active ingredient.

* * * * *